US012569477B2

(12) United States Patent
Andreeva et al.

(10) Patent No.: US 12,569,477 B2
(45) **Date of Patent: *Mar. 10, 2026**

(54) COMPOSITIONS FOR SYNERGISTICALLY ENHANCING MITOCHONDRIAL FUNCTION

(71) Applicant: MITOCHOLINE LTD, London (GB)

(72) Inventors: Larisa Andreeva, London (GB); Igor Anatolievich Pomytkin, Moscow (RU); Galina Nonina Skladtchikova, Hellemp (DK)

(73) Assignee: MITOCHOLINE LTD, London (GB)

( * ) Notice: Subject to any disclaimer, the term of this patent is extended or adjusted under 35 U.S.C. 154(b) by 422 days.

This patent is subject to a terminal disclaimer.

(21) Appl. No.: 18/091,167

(22) Filed: Dec. 29, 2022

(65) Prior Publication Data

US 2023/0181557 A1 Jun. 15, 2023

Related U.S. Application Data

(63) Continuation-in-part of application No. 18/051,460, filed on Oct. 31, 2022, now Pat. No. 11,826,362, which is a continuation of application No. 16/624,830, filed as application No. PCT/GB2018/051797 on Jun. 27, 2018, now Pat. No. 11,571,415.

(30) Foreign Application Priority Data

| | | |
|---|---|---|
| Jun. 28, 2017 | (GB) | 1710316 |
| Sep. 20, 2017 | (GB) | 1715214 |
| Jan. 8, 2018 | (GB) | 1800244 |
| May 12, 2018 | (GB) | 1807733 |

(51) Int. Cl.

| | |
|---|---|
| ***A61K 31/455*** | (2006.01) |
| ***A23L 33/13*** | (2016.01) |
| ***A23L 33/15*** | (2016.01) |
| ***A23L 33/17*** | (2016.01) |
| ***A61K 31/194*** | (2006.01) |
| ***A61K 31/197*** | (2006.01) |
| ***A61K 31/706*** | (2006.01) |
| ***A61K 47/16*** | (2006.01) |
| ***A61P 25/24*** | (2006.01) |
| ***A61P 25/28*** | (2006.01) |

(52) U.S. Cl.

CPC ............ *A61K 31/455* (2013.01); *A23L 33/13* (2016.08); *A23L 33/15* (2016.08); *A23L 33/17* (2016.08); *A61K 31/194* (2013.01); *A61K 31/197* (2013.01); *A61K 31/706* (2013.01); *A61K 47/16* (2013.01); *A61P 25/24* (2018.01); *A61P 25/28* (2018.01)

(58) Field of Classification Search

CPC .... A61K 31/14; A61K 31/154; A61K 31/197; A61K 31/455; A61K 31/456; A61K 31/706; A61K 45/06; A61K 47/16; A61K 2300/00; A61P 25/24; A61P 25/28; A23L 33/10; A23L 33/13; A23L 33/15; A23L 33/17

USPC ........................................................... 514/52

See application file for complete search history.

(56) References Cited

U.S. PATENT DOCUMENTS

| | | | | |
|---|---|---|---|---|
| 3,579,423 | A | 5/1971 | Yamane et al. | |
| 7,666,908 | B2 | 2/2010 | Pomytkin et al. | |
| 8,367,121 | B2 | 2/2013 | Mazzio et al. | |
| 8,673,977 | B2 | 3/2014 | Pomytkin | |
| 11,571,415 | B2 * | 2/2023 | Andreeva | A23L 33/15 |
| 11,826,362 | B2 * | 11/2023 | Andreeva | A61K 31/197 |
| 2006/0199862 | A1 * | 9/2006 | Pomytkin | A61K 31/205 514/554 |
| 2009/0214680 | A1 | 8/2009 | Giuliano et al. | |
| 2009/0258001 | A1 * | 10/2009 | Ponath | A61P 37/06 424/130.1 |
| 2015/0374745 | A1 | 12/2015 | Pomytkin et al. | |

FOREIGN PATENT DOCUMENTS

| | | | |
|---|---|---|---|
| WO | 2009022933 | A1 | 2/2009 |

OTHER PUBLICATIONS

McCandless, Cerebral Energy Metabolism and Metabolic Encephalopathy, 1985, pp. 313-329.*

AK Reeve et al., "Aggregated a-synuclein and complex I deficiency: exploration of their relationship in differentiated neurons", Cell Death and Disease (2015) 6, e1820; doi:10.1038/cddis.2015.166, Jul. 16, 2015, pp. 1-10.

S. Ogoh et al, "Cerebral blood flow during exercise: mechanisms of regulation", J Appl Physiol 107:. Sep. 3, 2009, pp. 1370-1380.

B. Hassel et al., "Cerebral dicarboxylate transport and metabolism studied with isotopically labelled fumarate, malate and malonate", Journal of Neurochemistry, 2002, pp. 410-419.

(Continued)

*Primary Examiner* — Ganapathy Krishnan

(74) *Attorney, Agent, or Firm* — Kunzler Needham & Hilton; Thomas D Briscoe

(57) ABSTRACT

Methods and compositions for reducing symptoms of mental concentration dysfunction, mood dysfunction, and/or stress-related dysfunction. In various examples, the methods include selecting a subject experiencing a symptom of mental concentration dysfunction, mood dysfunction, and/or stress-related dysfunction and providing for consumption by the subject, a nicotinamide composition formulated to reduce a frequency and/or severity of the symptom. The nicotinamide composition includes a first component and a second component. In some examples, the first component includes nicotinamide (NAM), nicotinamide riboside, or nicotinamide mononucleotide and the second component includes one or more compounds that provide a choline cation and a succinate anion (2−). In certain examples, the molar ratio of the choline cation:succinate anion (2−):first component is between 2:1:0.01 and 2:1:1.

12 Claims, 6 Drawing Sheets

(56) References Cited

OTHER PUBLICATIONS

SH Zeisel et al., "Choline: An Essential Nutrient for Public Health", Nutr Rev. Author manuscript; available in PMC, Nov. 25, 2009, pp. 1-14.
MJ Valenzuela et al., "Complex mental activity and the aging brain: Molecular, cellular and cortical network mechanisms", ScienceDirect, Brian Reserch Reviews, 2007, pp. 198-213.
ZI Storozjeva et al., "Dicholine salt of succinic acid, a neuronal insulin sensitizer, ameliorates cognitive deficits in rodent models of normal aging, chronic cerebral hypoperfusion, and beta-amyloid peptide-(25-35)-induced amnesia", BMC Pharmacology, Jan. 23, 2008, pp. 1-13.
T. Wallimann et al., "Intracellular compartmentation, structure and function of creatine kinase isoenzymes in tissues with high and fluctuating energy demands: the 'phosphocreatine circuit' for cellular energy homeostasis", Biochem J. vol. 281, 1992, pp. 21-40.
XH. Zhu et al., "In vivo NAD assay reveals the intracellular NAD contents and redox state in healthy human brain and their age dependences", PNAS vol. 122 No. 9, Mar. 3, 2015, pp. 2876-2881.
F. Bartolome et al., "Measurement of Mitochondrial NADH and FAD Autofl uorescence in Live Cells", Mitochondrial Medicine: vol. I, Probing Mitochondrial Function, 2015, pp. 263-270.
LD. Lukyanova et al., "Mitochondria-controlled signaling mechanisms of brain protection in hypoxia", Frontiers in Nueroscience, Oct. 1, 2015, pp. 1-15.
X. Chen et al., "Molecular and functional analysis of SDCT2, a novel rat sodium-dependent dicarboxylate transporter". The Journal of Clinical Investigation vol. 103, No. 8, Apr. 1999, pp. 1159-1168.
V. Knott et al., "Neurocognitive effects of acute choline supplementation in low, medium and high performer healthy volunteers", ScienceDirect, Pharmacology, Biochemistry and Behavior, Feb. 12, 2015, pp. 119-129.
PK.Shetty et al., "Nicotinamide pre-treatment ameliorates NAD(H) hyperoxidation and improves neuronal function after severe hypoxia", Neurobiol Dis Vo. 62, Feb. 2014, pp. 1-21.
B. Gong et al., "Nicotinamide riboside restores cognition through an upregulation of proliferator-activated receprot-y coactivator 1a regulated B-secretase 1 degradation and mitochondrial gene expression in Alzheimer's mouse models", ScienseDirect, Neurobiology of Aging, Jan. 9, 2013, pp. 1581-1588.
A. Vaarmann et al., "Novel pathway for an old neurotransmitter: Dopamine-induced neuronal calcium signalling via receptor-independent mechanisms", ScienceDirect, Cell Calcium vol. 48, Sep. 16, 2010, pp. 176-182.
C. Rae et al., "Oral creatine monohydrate supplementation improves brain performance: a double-blind, placebo-controlled, cross-over trial", The Royal Society, Aug. 13, 2003, pp. 2147-2150.
AP. Wojtovich et al., "Physiological consequences of complex II inhibition for aging, disease, and the mKATP channel", Biochim Biophys Acta, NIH Public Access, May 1, 2014, pp. 1-32.
PC. Hinkle, "P/O ratios of mitochondrial oxidative phosphorylation", ScienceDirect, Biochimica et Biophysica Acta, Sep. 2004, pp. 1-11.
IA. Pomytkin et al., "Study of the Effect of Preconditioning with Succinic Acid Salt of Choline (1:2) on the Disturbances of Energy Metabolism in the Brain during Ischemia by 31 P NMR In vivo", Doklady Biochemistry and Biophysics, vol. 403 No. 3, Dec. 15, 2004, pp. 289-292.
BH. Cline et al., "The neuronal insulin sensitizer dicholine succinate reduces stress-induced depressive traits and memory deficit: possible role of insulin-like growth factor 2", BMC Neuroscience, 2002, pp. 1-14.
H. Imamura et al, "Visualization of ATP levels inside single living cells with fluorescence resonance energy transfer-based genetically encoded indicators", PNAS vol. 106 No. 37, Sep. 15, 2009, pp. 15651-15656.
"WHO Model List of Essential Medicines" 19th Edition, Apr. 2015, pp. 1-51 (55).
M. Gerlach et al., Altered Brain Metabolism of Iron as a Cause of Neurodegenerative Diseases?, Journal of Neurochemistry vol. 63, No. 3, 1994, pp. 793-807.
D. Kapogiannis et al., "Disrupted energy metabolism and neuronal circuit dysfunction in cognitive impairment and Alzheimer's disease", Lancet Neurology vol. 10, Feb. 2011, pp. 187-198.
McCandless et al., "Cerebral Energy Metabolism and Metabolic Encephalopathy", Departments of Anesthesia and Physiology, The Milton S. Hershey Medical Center, The Pennsylvania State University College of Medicine, Hershey, Pennsylvania 17033, 1985, pp. 1-458.
M. Hargreaves et al., "Skeletal muscle energy metabolism during exercise" Nature Metabolism vol. 2, Sep. 2020, pp. 817-828.
A. Leyssens et al., "The relationship between mitochondrial state, ATP hydrolysis, [Mg2+]i and [Ca2+]i studied in Isolated rat cardiomyocytes", The Journal of Physiology, 496.1, Oct. 1, 1996, pp. 111-128.
A. Moretti et al., "Choline: An Essential Nutrient for Skeletal Muscle", Nutrients, MDPI, Jul. 18, 2020, pp. 1-11.
A. Reddy et al., "pH-Gated Succinate Secretion Regulates Muscle Remodeling in Response to Exercise", Cell vol. 183 Issue 1, Oct. 1, 2020, pp. 62-75.

* cited by examiner

COMPOSITIONS FOR SYNERGISTICALLY ENHANCING MITOCHONDRIAL FUNCTION

CROSS-REFERENCES TO RELATED APPLICATIONS

The present application is continuation-in-part of U.S. application Ser. No. 18/051,460 titled "Composition For Enhancing Mitochondrial Function" and filed Oct. 31, 2022. U.S. application Ser. No. 18/051,460 is a continuation of U.S. application Ser. No. 16/624,830 titled "Composition For Enhancing Mitochondrial Function" and filed on Dec. 19, 2019, which is a U.S. National Stage Entry of and claims the priority to PCT/GB2018/051797 titled Composition and filed on Jun. 27, 2018, and claims priority to GB 1800244.4 filed on Jan. 8, 2018, GB 1715214.1 filed Sep. 20, 2017, GB 1710316.9 filed on Jun. 20, 2017, and GB 1807733.9 filed on May 12, 2017, each of which is incorporated herein by reference to the extent permitted by applicable patent law and rules.

FIELD

This disclosure relates generally to compositions and methods for enhancing mitochondrial function.

BACKGROUND

Mitochondria play various important roles in human cells such as producing adenosine triphosphate (ATP) for providing energy to cells, storing, and regulating calcium, generating heat, facilitating normal apoptosis, and aging processes. Mitochondrial dysfunction may be present from birth or may occur at any age and may affect cells in many parts of the body including the brain, muscles, internal organs, sensory organs, and more.

SUMMARY

Methods and compositions are disclosed for reducing symptoms of mental concentration dysfunction, mood dysfunction, and/or stress-related dysfunction. In some examples, the symptom of mental concentration dysfunction includes lack of mental concentration, lack of mental endurance, loss of focus, and/or mental fatigue. In other examples, the symptom of mood dysfunction comprises at least one of includes mood swings, bad mood, mental depression, and/or seasonal affective disorder. In still other examples, the symptom of stress-related dysfunction includes insomnia and/or mental stress.

Some implementations of a method in accordance with the disclosure include selecting a subject experiencing a symptom of mental concentration dysfunction, mood dysfunction, and/or stress-related dysfunction. In some representations, the method may include providing for consumption by the subject, a nicotinamide composition formulated to reduce a frequency and/or severity of the symptom.

Some representations of the nicotinamide composition include a first component and a second component. The first component includes nicotinamide (NAM), nicotinamide riboside, or nicotinamide mononucleotide, for example. The second component includes one or more salts that provide a choline cation and a succinate anion (2−). In some implementations, the molar ratio of the choline cation:succinate anion (2−):first component is between 2:1:0.01 and 2:1:1.

According to a first aspect of the disclosure, the second component comprises dicholine succinate (DiSU). In one example, an effective amount of the nicotinamide composition comprises between 10 mg and 1000 mg of DiSU. In another example, an effective amount of the nicotinamide composition comprises between 10 mg and 4000 mg of the first component. According to another aspect of the disclosure, the second component includes choline bitartrate and/or succinic acid disodium salt. In some examples, the nicotinamide composition further includes creatine or a creatine precursor.

In some implementations, an effective amount of the nicotinamide composition is provided for consumption by the subject such that the molar ratio of the nicotinamide composition synergistically increases an adenosine triphosphate (ATP) level, a phosphocreatine (PCr) level, and/or a nicotinamide adenine dinucleotide (NADH) level in the subject.

BRIEF DESCRIPTION OF THE FIGURES

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Figure 1A:
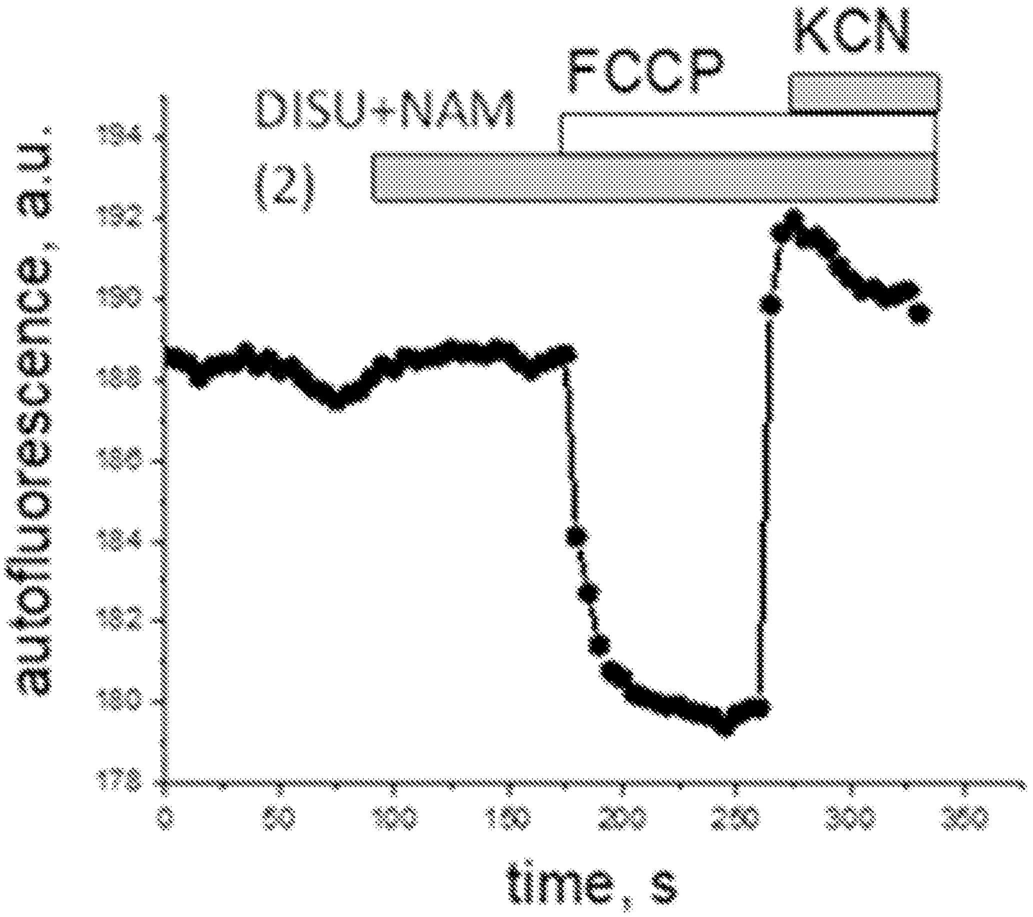
FIG. 1A shows NADH autofluorescence levels in mitochondria as an illustration in connection with Example 7.

Reference throughout this specification to "one example," "an example," or similar language means that a particular feature, structure, or characteristic described in connection with the implementation is included in at least one example of the present disclosure. Thus, appearances of the phrases "in one example," "in an example," and similar language throughout this specification may, but do not necessarily, all refer to the same example.

Introduction

Human body cells, especially in the brain, are dependent on oxygen for adenosine triphosphate (ATP) production in mitochondria. Nicotinamide adenine dinucleotide (NAD) is a coenzyme that serves as a hydrogen carrier NADH/NAD+ between substrates of tricarboxylic acid cycle and complex I mitochondria supporting thus ATP production during the oxidative phosphorylation. At normoxia (e.g., normal oxygen supply), NADH oxidation at mitochondrial complex I contributes to about 90% of total oxygen consumption. Nicotinamide (CAS No. 98-92-0) is a precursor of NAD+/NADH and the vitamin B3. Nicotinamide is found in food and used as a dietary supplement. Nicotinamide is also included in the list of essential medicines needed for health.

Nicotinamide incubation (5 mM) of fresh brain tissue slices two hours prior to hypoxia (a condition of a deficiency in oxygen supply of tissues of the body) significantly increases total NAD(H) content, improves neuronal recovery, enhances ATP content, and prevents NADH hyperoxidation.

Succinic acid or salts thereof (succinates) are substrates of mitochondrial complex II. At hypoxia, succinate oxidation may contribute to 70-80% of total oxygen consumption. Because of high acidity (pKa1=4.2 and pKa2=5.6), fumaric acid is dissociated completely at physiological range of pH 7.0-7.8 and is present in the body as dicarboxylate-anion (succinate).

Succinate transport across the body is mediated by specific sodium-coupled dicarboxylate-anion transmembrane transporters of solute carrier family 13 (SLC13). However, there is no specific transporting system for succinic acid or salts thereof across the blood-brain barrier (BBB), since no dicarboxylate-anion transporters are found in cerebral blood vessels or the choroid plexus. Moreover, dicarboxylates cannot penetrate the BBB. Because of lack of transport capacity across the BBB, orally administered succinic acid and salts thereof generally are not effective in the treatment of disorders of central nervous system (CNS).

Choline salt of succinic acid (2:1) (hereinafter DiSU or choline succinate (2:1) salt) is a specific salt of succinic acid that has been demonstrated to be surprisingly effective in the treatment of CNS disorders and enhancing cognitive function in animals. Further, it has been demonstrated that DiSU salt is able to slow whole-brain ATP decline. In particular, DiSU has a protective effect on the brain energy metabolism during global ischemia. Treatment with DiSU may preserve cognitive function in animals in a model of chronic cerebral hypoperfusion.

Choline is an essential nutrient for healthy metabolic functioning. Choline is needed for biosynthesis of acetylcholine and as a neurotransmitter crucial for communication of neurons in the nervous system. Choline deficiency leads to neurological disorders, while oral administration of choline enhances cognitive function in relatively impaired performers. An adequate intake level for choline is 550 mg/day for men and 425 mg/day for women. De novo choline synthesis, however, is not sufficient to meet human requirements. Instead, choline must be obtained through a diet containing choline-rich foods, like eggs and shrimps, or as a nutritional supplement to a normal diet, for example in the form of choline salts.

Aging often results in a physiological cerebral hypoxia, e.g., a deficiency in oxygen supply of the brain, due to a decrease of cerebral blood flow by approximately 28-50% from age of 30 to 70 years. NAD+ availability and abnormal NAD+/NADH redox state are also tightly linked to aging and age-related metabolic diseases and neurodegenerative disorders. Based on results of several studies it has been suggested that mitochondrial complex II plays an important role in aging.

In various examples, a composition for enhancing mitochondrial function includes choline cation, succinate anion (2−), nicotinamide, and/or a nicotinamide derivate, such as for example, nicotinamide riboside and nicotinamide mononucleotide. In certain examples, a composition for enhancing mitochondrial function includes choline cation, succinate anion (2−) and nicotinamide, or a nicotinamide derivate for use in maintaining or enhancing the brain energy metabolism in a human. In some examples, a composition in accordance with the disclosure consists of choline cation, succinate anion (2−) and nicotinamide, or a nicotinamide derivate for use enhancing cognition, learning and/or memory, mental strength, and endurance in a human.

In some aspects, a composition for enhancing mitochondrial function includes choline cation, succinate anion (2−), and nicotinamide, or a nicotinamide derivate for use in the dietary management of one or more symptoms and conditions associated with an imbalanced, damaged or reduced brain energy metabolism.

In other aspects, methods are presented for the dietary management of a symptom or condition associated with an imbalanced, damaged, or reduced brain energy metabolism in a human. In still other aspects, methods are presented for the dietary prevention of developing, occurring and/or reoccurring of a symptom or condition associated with an imbalanced, damaged, or reduced brain energy metabolism in a human, including administering to a human, at least once a day, a composition including choline cation, succinate anion (2−) and nicotinamide, or a nicotinamide derivate.

In some examples, the molar ratio of choline cation, succinate anion (2−) and nicotinamide, or the nicotinamide derivate, in the composition is preferably in a range from about 2:1:0.01 to about 2:1:10. The choline cation and succinate anion (2−) may derive from one and the same salt, in particular, choline succinate (2:1) salt, or from two different salts, e.g., choline bitartrate and succinate disodium salt. In one preferred embodiment, the composition is a nutritional composition or a part of a nutritional composition.

Preferably, the composition is administered to a human daily in one or more doses for a period of one or more days. The human may be an aging human individual and/or a human individual who is having or who is susceptible to psychological stress, fatigue, insomnia, or mental depression.

One or more symptoms associated with an imbalanced, damaged, or reduced brain energy metabolism in a human may include lack of mental concentration, weakened mental strength and endurance, frequent mood swings, mental depression, seasonal affective disorder (SAD), insomnia, fatigue, weakened cognitive capacity, learning and memory.

In some implementations, a combination of choline cation, succinate anion (2−) and nicotinamide, or a nicotine derivate, may be utilized in a human for restoring, maintaining and/or enhancing brain energy metabolism; restoring, maintaining and/or enhancing mental and physical endurance; maintaining and/or enhancing cognitive functions; treating or reducing the risk of development or reoccurrence of a condition or a symptom associated with an imbalanced, damaged or reduced brain energy metabolism; and/or treating or reducing the risk of or delaying the onset of cognitive impairment associated with associated with an imbalanced, damaged or reduced brain energy metabolism.

The human may be any human individual. In some implementations, the human is an aging human individual and/or a human individual who is having or susceptible to psychological stress, fatigue, insomnia, or mental depression.

All terms and definitions explained throughout the text of specification relate to all aspects and implementations, unless otherwise specified.

As used herein, a list with a conjunction of “and/or” includes any single item in the list or a combination of items in the list. For example, a list of A, B and/or C includes only A, only B, only C, a combination of A and B, a combination of B and C, a combination of A and C or a combination of A, B and C.

As used herein, a list using the terminology “one or more of” includes any single item in the list or a combination of items in the list. For example, one or more of A, B and C includes only A, only B, only C, a combination of A and B, a combination of B and C, a combination of A and C or a combination of A, B and C. As used herein, a list using the terminology “one of” includes one and only one of any single item in the list. For example, “one of A, B and C” includes only A, only B or only C and excludes combinations of A, B and C. As used herein, “a member selected from the group consisting of A, B, and C,” includes one and only one of A, B, or C, and excludes combinations of A, B, and C.

As used herein, “a member selected from the group consisting of A, B, and C and combinations thereof” includes only A, only B, only C, a combination of A and B, a combination of B and C, a combination of A and C or a combination of A, B and C.

The present disclosure relates to synthetic compositions that are safe and effective to maintain and enhance energy metabolism and particularly the brain energy metabolism in humans. The compositions can be used to support or re-establish a proper brain energy metabolism and to help to enhance the physical and mental endurance in a human, including healthy human individuals and individuals diagnosed with a disease, without age limitation and in a combination with any diet and/or therapy. According to certain implementations, the compositions include at least three compounds associated with energy metabolism.

For example, some compositions disclosed herein consist essentially of three compounds: choline cation, succinate anion (2−), and nicotinamide (NAM), preferably in a molar ratio between about 2:1:0.01 to about 2:1:10. In some examples, the choline cation and the succinate anion are present in the composition in the form of a choline succinate salt, preferably choline succinate (2:1) salt (interchangeably termed herein “di-choline succinate” or “DiSU”). The term “(2:1)” in the present context means a single molecule of the choline succinate salt comprises two choline cations and one succinate anion (2−). In some representations, the composition includes a derivate of NAM as an alternative NAM.

Surprisingly, the present inventors found that a synthetic composition consisting of choline cation, succinate anion (2−) and nicotinamide, exogenously added to mammalian brain cells in vitro, is synergistically effective for increasing the level of both nicotinamide adenine dinucleotide (NADH) and adenosine triphosphate (ATP) in the cells. An especially enhanced production of NADH and ATP in mitochondria of the brain cells was observed when the choline cation and succinate anion (2−) were derived from di-choline succinate salt (DiSU) present in the composition. However, a significant enhancement of the production of ATP and NADH could also be achieved when the choline cation and succinate anion of the composition were derived from other salts of comprising said cation and anion.

Furthermore, the inventors found that human individuals treated with an aqueous composition including DiSU and NAM observed at least one of the following effects: reduced symptoms of seasonal affective disorder (SAD), decreased symptoms of fatigue, decreased frequency and scale of mood swings, decreased psychological depression and stress, as well as an increased prevalence of good mood and well-being feeling, better mental concentration, more clarity and endurance of mind. Moreover, there has been recorded a persistent increase in the level of cellular energy deport phosphocreatine (PCr) in the brain of a human individual in vivo following two weeks of intake of a Beverage including the combination of DiSU and NAM disclosed herein.

The wording “consisting of” and “consisting essentially of” does not exclude other compounds from inclusion in the composition.

The term “synthetic” may include both synthetically prepared molecules that are structurally identical to molecules that naturally occur in living bodies, as well as artificial molecules that do not have natural structural equivalents.

The term “about” means a deviation from the indicated value by 0.01% to 10%, such as from 0.5% to 5%.

The term “choline cation” means the cation having the chemical formula C5H14NO+ (CAS No. 62-49-7). The term “succinate anion” means succinic add anion (2−) having the chemical formula C4H4O4−2 (CAS No. 110-15-6), The terms “di-choline succinate”, “choline succinate salt (2:1)” and “DiSU” are interchangeable and refer to the molecule of formula (I):

(I)

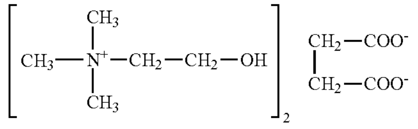

The term “nicotinamide” or “NAM” means the molecule identified as CAS No. 98-92-0.

The term “derivate of nicotine amide” or “NAM derivate” means a molecule that is derived from NAM by a synthetic process, e.g., NAM is a start molecule for the synthesis of the derivate, e.g., nicotinamide riboside (CAS No: 1341-23-7) or nicotinamide mononucleotide (CAS No: 1094-61-7).

As mentioned above, a first aspect of the invention relates to a composition including choline cation, succinate anion (2−), and NAM or a NAM derivate. In certain implementations, the choline cation and succinate anion are present in the molar ratio 2:1 and may be present in the form of choline succinate salt (2:1) (DiSU). Alternatively, the choline cation of the composition may derive from another salt of choline, e.g., choline bitartrate (CAS No. 87-67-2), and succinate anion may derive from another salt of succinic acid, e.g., succinic acid disodium salt (CAS No. 6106-21-4). Some representations of the composition may include choline bitartrate, succinic acid disodium salt and NAM. As mentioned, the molar ratio of choline cation, succinate anion (2−) and NAM in the composition may vary from about 2:1:0.01 to about 2:1:10. In other implementations, the molar ratio of choline cation, succinate anion (2−) and NAM in the composition may vary from about 2:1:0.01 to about 2:1:1.

Compositions with a molar ratio of individual compounds within these ranges act synergistically and enhance the production of major energy molecules such as adenosine triphosphate (ATP), phosphocreatine (PCr), and nicotinamide adenine dinucleotide (NADH) in brain cells. Further, these compositions are efficient in dietary management of symptoms of seasonal affective disorder (SAD), mood swings, insomnia, fatigue, weakened mental concentration and endurance, psychological stress, and depression in humans, which symptoms are typically associated with imbalanced or weakened energy metabolism. Some implementations of the composition may include the compound ratios described in the working examples below. The example compositions are not limiting. however, as implementations of the composition have the energy generating effect described herein throughout the entire ratio range.

To obtain the above effects for the purposes described herein, the compounds of the composition, e.g., choline cation, succinic acid anion (2−) and NAM, or a NAM derivate, are present in so called "effective amounts". The effective amounts of the compounds may vary depending on the aim and/or method of use, and on the target subject. Some non-limiting working examples are discussed below.

In some embodiments, a composition including choline cation, succinate anion (2−) and NAM may further include creatine (CAS No. 57-00-1) or a creatine precursor, such as amino acids glycine and arginine. Other useful additives to a composition comprising choline cation, succinate anion (2−) and NAM or a NAM derivate are discussed below.

Representative compositions may be used for maintaining, establishing or re-establishing a proper level of brain energy metabolism in a human, where "proper level of brain energy metabolism" refers to a dynamic capability of the brain cells to generate energy by producing biological "energy" molecules NADH, ATP and PCr in amounts sufficient to maintain normal brain functioning, including processes related to cognition, learning, memory, mental focus and endurance, and the like under normal conditions.

In some implementations, the amounts may be selected to compensate for increased energy consumption by brain processes under extraordinary conditions, such as in situations characterized by an extraordinary overload or complexity of mental tasks, or demanding an increased mental and/or physical endurance, performance, or the like. A level of brain energy metabolism may differ from one human to another, and may depend on age, education level, social status, health status, mental capability, or physical capability, for example. The brain energy metabolism level may be defined according to existing standards for mental performance.

In some examples, the composition provides an extraordinary support in generation of energy, e.g., generation of energy-providing molecules NADH, ATP and PCr, to an energy-depleted and weakened brain (e.g., due to a disease, age, environmental or psychological factors). For the maintaining, establishing, or re-establishing a proper level of brain energy metabolism in a human, the composition can be used as an everyday dietary supplement both by healthy individuals and medical patients, as it is safe to use in a combination with any diet and medicaments.

Advantageously, in one embodiment, the composition may be used for maintaining or enhancing the brain energy metabolism in an aging human. The term "aging human" in the present context generally relates to a human individual of 14 years old or older, preferably, a human individual over 24-25 years old. In another embodiment, the composition can be advantageously used for the prophylaxis of aging of the brain. It is well known that the energy generating capability of the brain gradually diminishes with aging. Used on everyday basis for maintaining a proper brain energy metabolism by a human individual at earlier age, including infants and young children, the composition has an advantageous capability to maintain the speed and complexity of energy-demanding processes of the brain unchanged through the life span of the individual, or, at least, it can decrease the speed of brain aging associated with the depletion of energy deports by persistently fueling the aging brain with energy and allowing the aging brain to perform on the level of a young brain.

Some implementations of the compositions may be formulated as nutritional compositions. Such compositions may include effective amounts of the ingredients of the composition in nutraceuticals, in an appropriate molar ratio as described above.

The term "nutraceutical" means a pharmaceutical-grade and standardized nutrient. The term "nutrient" means in the present context substance that provides nourishment essential for the maintenance of life of a human. The term "nutritional" in the present context means that the composition is for the dietary supplementation of a human individual. The term "dietary supplement" means a product taken by mouth that contains a dietary ingredient, e.g., a nutrient, intended to supplement the diet.

The term "human" as used herein relates to any human individual. In some examples, the human is an aging human, such as an individual over 24-25 years old, over 30 years old, between 35 and 55 years old, or between 40 and 60 years old. In another example, the human is an individual who is having or who is susceptible to psychological stress, fatigue, insomnia, or mental depression. In one example, the human is an aging individual who is having or who is susceptible to a psychological stress, fatigue, insomnia, or mental depression.

The amounts of choline cation, succinate anion (2−) and NAM, e.g., DiSU and NAM, in a composition may be adjusted for use by a particular individual or a group of individuals according to the individual's needs, age, physiological conditions, etc., and depending on the dosage form and administration regime For example, the amount of NAM in the composition may vary from 10 mg to 4000 mg per serving, served as one or more dosages a day, such as about 25-2000 mg per serving, served as several dosages per day, or about 50-1000 mg per serving served as several dosages per day, etc., wherein the daily dose of NAM will depend on the dietary demand of a concrete human individual or a group of human individuals. Some dietary compositions useful for some specific demands are described in non-limiting working examples. However, a daily intake of about 4000 mg of NAM in the composition is considered as safe and effective for any described herein purpose.

The amount of DiSU per serving may vary from 10 mg to 1000 mg per serving, and it can be served as one or more dosages a day. Accordingly, to archive a desired effect, as any of the described herein, without having any negative physiological effects, an individual may intake a composition comprising up to 4000 mg NAM, or a NAM derivate, and up to 1000 mg DiSU, or the corresponding amounts of choline cation and succinate (2−) anion derived from other salts of choline and succinic acid, daily. In one example, a nutritional composition includes DiSU and NAM, and the molar ratio of choline cation, succinate anion (2−) and nicotinamide in the composition is about 2:1:0.4, correspondingly. In another example, the molar ratio of choline cation, succinate anion (2−) and nicotinamide in the composition is about 2:1:1.

The term "about" in the present context means a 1-10% deviation from the indicated value. Preferably, the intake is continuous for a period of at least one week or for a longer period of time, such as 2 to 4 weeks, 1 to 12 months, or longer. There is practically no limit for how long the composition can be taken as a dietary supplement. The intake can be interrupted any time for a period of time and resumed again when the individual feels that it is needed, e.g., in connection with changes in individual's life, health, seasonal fluctuations of individual's physiological/mental state, or age. A dietary manager of ordinary skill can readily determine the amounts of said ingredients of the dietary composition according to the accepted rules and regulations.

In further aspects, implementations of the composition may be utilized (i) for restoring, maintaining or enhancing the brain energy metabolism in a human; (ii) for enhancing concentration, attentiveness, mental strength and endurance, cognition, learning and/or memory in a human; (iii) for treating and/or reducing the symptoms of psychological stress, lack of mental concentration, weakened mental strength and endurance, frequent mood swings, mental depression, seasonal affective disorder (SAD), insomnia, fatigue; (iv) for delaying the onset of brain aging associated with a decline of the brain capability of generating energy molecules, such as NADH, ATP and PCr, necessary for energy-demanding processes relating to performing complex metal tasks, cognition, learning, memory, attentiveness, focus, and the like. As used herein, the term "mental strength" means the ability of an individual to regulate his or her thoughts, control emotions, and behave productively despite the circumstances. The term "mental endurance" means the ability to exercise mental strength in everyday life, and the ability to deal effectively with all challenges.

Accordingly, a combination of choline cation, succinate anion (2−) and nicotinamide or a nicotine derivate as described herein may be utilized in a human for restoring, maintaining and/or enhancing brain energy metabolism; restoring, maintaining and/or enhancing mental and physical endurance; maintaining and/or enhancing cognitive functions; treating or reducing the risk of development or re-occurrence of a condition or a symptom associated with an imbalanced, damaged or reduced brain energy metabolism; treating or reducing the risk of or delaying the onset of cognitive impairment associated with associated with an imbalanced, damaged or reduced brain energy metabolism in said human is beneficial and safe, independently whether this combination a part of a composition comprising a broad spectrum other compounds (e.g., such as described below) or as a solo composition essentially comprising a salt of choline, providing the choline cation, a salt of succinic acid, providing the succinate (2−) anion, and nicotine amine or a nicotine amide derivate as described herein.

The term "cognitive impairment" in the present context means "mild cognitive impairment (MCI)" that is characterized by a slight but noticeable and measurable decline in cognitive abilities, including memory and thinking skills. A person with MCI is at an increased risk of developing Alzheimer's or another dementia. The term "restoring" is used interchangeably with the term "re-establishing" and means bringing back to or putting back into a former or original state.

Aspects of compositions described herein also include methods of dietary management of symptoms and conditions associated with imbalanced, damaged, or reduced brain energy metabolism, lack of mental concentration, weakened mental strength and endurance, frequent mood swings, mental depression, seasonal affective disorder (SAD), insomnia, fatigue, weakened cognitive capacity, learning and memory, said methods comprising a step of administration of a composition to a human subject. The term "dietary management" in the present context means the practice of providing a nutritional option for individuals and groups with health concerns instead of a therapeutic intervention or as a prophylactic treatment, preferably under supervision of a dietary or medical professional.

Advantageously, implementations of compositions set forth herein can be used as a dietary prophylaxis of primary and/or secondary development or in response to occurrence of a symptom or condition associated with an imbalanced, damaged, or reduced brain energy metabolism in a human. In some implementations, the compositions may be used to reduce the risk of occurrence and re-occurrence of the same symptom or condition and/or reduce the strength and/or duration of the symptom or condition. Accordingly, one aspect of a method in accordance with the disclosure relates to providing dietary prevention of a symptom or condition associated with an imbalanced, damaged, or reduced brain energy metabolism in a human.

The term "imbalanced, damaged or reduced" in the present context means that an individual's brain energy metabolism is not on a proper level (as discussed above), but is weakened by a disease, physiological or psychological condition of the individual, harmful environmental factors.

As mentioned above, some implementations relate to nutritional compositions including nutrients other than essential compounds. For example, a nutritional composition may be in the form of a nutritional product including without limitation a food, a Beverage, a dietary supplement, a functional food, and a medical food. In one representation, a composition is an aqueous nutritional composition such as a drink or Beverage.

In practicing methods and compositions herein, the compounds of the composition can be prepared by any process known in the art or obtained from a known commercial manufacturer. For example, nicotinamide or its derivatives choline bitartrate and succinate disodium salt, may be obtained from Merck. DiSU can be prepared by the reaction of choline hydroxide (CAS No. 123-41-1) with succinic acid (CAS No. 110-15-6).

Some implementations of nutritional compositions described herein may be prepared by procedures well-known in the art and may contain additional optional ingredients.

Optional ingredients are generally included in amounts ranging from about 0.0005% to about 10.0% by weight of the composition. Examples of suitable optional ingredients include, but are not limited to, carriers, minerals, carbohydrates, lipids, vitamins, co-factors, buffers, flavors and sweeteners, inorganic salts, cations and anions typically abandoned in natural drinking water, taste modifying and/or masking agents, carbon dioxide, amino acids, organic acids, antioxidants, preservatives, and colorants. The nutritional compositions can be combined with one or more carriers and used in the form of ingestible tablets, buccal tablets, troches, capsules, elixirs, suspensions, syrups, wafers, chewing gums, foods, Beverages, and the like.

Non-exclusive examples of ingredients which can serve as carriers include water; sugars, such as glucose, lactose, and sucrose; cellulose, and its derivatives; starches, such as corn starch and potato starch; powdered tragacanth; malt; gelatin; talc; excipients, such as cocoa butter; oils, such as olive oil, peanut oil, cottonseed oil, corn oil and soybean oil; glycols, such as propylene glycol; esters, such as ethyl oleate and ethyl laurate; polyols, such as glycerin, mannitol, sorbitol, and polyethylene glycol; agar; buffering agents; water; pH buffered solutions; and other non-toxic compatible substances employed in formulations.

Wetting agents, emulsifiers, and lubricants, such as sodium lauryl sulfate and magnesium stearate, as well as coloring agents, release agents, coating agents, sweetening, flavoring and perfuming agents, preservatives and antioxidants can also be present in the compositions. Non-exclusive examples of antioxidants are Vitamin E, ascorbic acid, carotenoids, aminoindoles, Vitamin A, uric acid, flavonoids, polyphenols, herbal antioxidants, melatonin, lipoic acids, and mixtures thereof. Non-exclusive examples of useful inorganic salts typically abandoned in natural drinking water are sodium carbonate, sodium bicarbonate, potassium chloride, magnesium chloride, calcium chloride, and mixtures thereof. Non-exclusive examples of useful cations are sodium, potassium, magnesium, calcium, zinc, iron, and mixtures thereof. Non-exclusive examples of useful anions are fluoride, chloride, bromide, iodide, carbonate, bicarbonate, sulfate, phosphate, and mixtures thereof.

Non-exclusive examples of suitable buffers are phosphate buffer, glycine buffer, citrate buffer, acetate buffer, carbonate buffer, tris-buffer, triethanolamine buffer, and succinate buffer.

Non-exclusive examples of suitable flavors are synthetic flavor oils; flavoring aromatics and naturals oils such as cinnamon oil, oil of wintergreen, peppermint oils, clove oil, bay oil, anise oil, eucalyptus, thyme oil, cedar leave oil, oil of nutmeg, oil of sage, oils of citrus fruits, oil of bitter almonds, and cassia oil; plant extracts, flowers, leaves, fruits, vanilla, chocolate, mocha, coffee, apple, pear, peach, citrus such as lemon, orange, grape, lime, and grapefruit; mango, strawberry, raspberry, cherry, plum, pineapple, and apricot, and combinations thereof.

Non-exclusive examples of suitable sweeteners are natural and synthetic sweeteners. Non-exclusive examples of natural sweeteners are naturally occurring substances, sucrose, extracts from naturally occurring substances; extracts of the plant *Stevia rebaudiana* Bertoni such as *stevia*, steviol, rebaudiosides A-F, and dulcosides A and B; extracts of *Thladiantha grosvenorii* such as mogroside V and related glycosides and triterpene glycosides; phyllodulcin and its derivatives; thaumatin and its derivatives; mogrosides such as mogroside IV, mogroside V, siamenoside, and mixtures thereof; genus *Siraitia* including *S. grosvenorii, S. siamensis, S. silomaradjae, S. sikkimensis, S. Africana, S. borneesis*, and *S. taiwaniana*; naturally-occurring glycosides; and active compounds of plant origin having sweetening properties, and mixtures thereof. Non-exclusive examples of synthetic sweeteners are aspartame saccharin, and mixtures thereof.

Non-exclusive examples of suitable colorants are dyes suitable for food such as those known as FD&C dyes, natural coloring agents such as grape skin extract, beet red powder, titanium dioxide, and beta-carotene, annatto, carmine, chlorophyll, paprika, and mixtures thereof.

Non-exclusive examples of useful organic acids are acetic acid, butyric acid, malic acid, pyruvic acid, glutamic acid, citric acid, omega-3 unsaturated acids, linoleic acid, linolenic acid, eicosapentaenoic acid, docosahexaenoic acid, aspartic acid, and mixtures thereof.

Non-exclusive examples of useful amino acids are glycine, arginine, 1-tryptophan, 1-lysine, methionine, threonine, levocarnitine, and 1-carnitine.

Non-exclusive examples of useful vitamins are thiamin, riboflavin, nicotinic acid, panthothenic acid, biotin, folic acid, pyridoxine, vitamin B12, lipoic acid, vitamin A, vitamin D, vitamin E, ascorbic acid, choline, carnitine; alpha, beta, and gamma carotenes; vitamin K, and mixtures thereof.

Non-exclusive examples of useful co-factors are thiamine pyrophosphates, flavin mononucleotide, flavin adenine dinucleotide, pyridoxal phosphate, biotin, tetrahydrofolic acid, Coenzyme A, coenzyme B12, 11-cis-retinal, 1,25-dihydroxycholecalciferol and mixtures thereof.

One example of a nutritional composition includes compounds that increase blood circulation such as an extract of *Ginkgo biloba* or ginseng. In some examples, a composition may include one or more anti-oxidants such as astaxanthin, resveratrol, or flavonoids. In some implementations, the nutritional compositions can be used as a component of a food product. Non-exclusive examples of food products include regular foods, dietary supplements, Beverages, and medical foods, such as those formulated to be consumed or administered enterally under the supervision of a physician and intended for specific dietary management of a disease, condition, or disorder.

Some implementations of the nutritional compositions are administered to a human orally for a period of at least one day or longer, as discussed above.

The following non-limiting working examples are illustrative of the methods and compositions disclosed herein. The working examples are not limiting of the scope of the methods or compositions in any way.

Example 1

Embodiments of Nutritional Compositions

Beverage 1. The Beverage is prepared by mixing of NAM with DiSU in amounts as indicated below and dissolved in 330 ml of water to provide a Beverage.

Beverage 1

| Ingredient | Content, per serving |
|---|---|
| NAM | 37 mg |
| DiSU | 250 mg |
| Succinic acid (or D-gluconic acid (for e.g., Ex. 7-9) | qs to pH 6.5 |
| Water | to 330 ml |

This Beverage (molar ratio choline:succinate:NAM is 2:1:0.4), when administered orally to a subject daily, 330 ml per serving, one or more servings, is useful for improvement of brain energy metabolism in a subject, helping the subject to maintain high mental endurance and persistent feeling of well-being.

Beverage 2. The Beverage is prepared by mixing of NAM with DiSU in amounts as indicated below and dissolved in 330 ml of water.

Beverage 2

| Ingredient | Content, per serving |
|---|---|
| NAM | 188 mg |
| DiSU | 250 mg |
| Succinic acid (or D-gluconic acid (for e.g., Ex. 7-9) | qs to pH 6.5 |
| Water | to 330 ml |

This Beverage (molar ratio choline:succinate:NAM is 2:1:2), when administered orally to a subject daily, 330 ml per serving, one or more servings, is useful for dietary management of disorders accompanying cerebral hypoxia and psychological stress.

Beverage 3. The Beverage is prepared by mixing of NAM with DiSU in amounts as indicated below and dissolved in 330 ml of water.

Beverage 3

| Ingredient | Content, per serving |
|---|---|
| NAM | 188 mg |
| DiSU | 500 mg |
| Succinic acid (or D-gluconic acid for e.g., Ex. 7-9) | qs to pH 6.5 |
| Water | to 330 ml |

This Beverage (molar ratio choline:succinate:NAM is 2:1:1), when administered orally to a subject daily, 330 ml per serving, one or more servings, is useful for improvement of brain energy reserve, as measured by phosphocreatine-to-ATP ratio.

Beverage 4. The Beverage is prepared by mixing of NAM with DiSU in amounts as indicated below and dissolved in 500 ml of water.

Beverage 4

| Ingredient | Content, per serving |
|---|---|
| NAM | 210 mg |
| DiSU | 560 mg |
| D-gluconic acid (for e.g., Ex. 7-9) | qs to pH 6.5 |
| Water | to 500 ml |

This Beverage (molar ratio choline:succinate:NAM is 2:1:1), when administered orally to a subject daily, 500 ml per serving, one or more servings, is useful for balancing the brain energy to the level that is necessary for healthy brain functioning.

Beverage 5. The Beverage is prepared by mixing of NAM with DiSU in amounts as indicated below and dissolved in 330 ml of water.

Beverage 5

| Ingredient | Content, per serving |
|---|---|
| NAM | 375 mg |
| DiSU | 100 mg |
| Succinic acid (or D-gluconic acid for e.g., Ex. 7-9) | qs to pH 6.5 |
| Water | to 330 ml |

This Beverage (molar ratio choline:succinate:NAM is about 2:1:10), when administered orally to a subject daily, 330 ml per serving, one or more servings, is useful for enhancing of brain healthy functioning.

Beverage 6. The Beverage is prepared by mixing of NAM with DiSU in amounts as indicated below and dissolved in 330 ml of water.

Beverage 6

| Ingredient | Content, per serving |
|---|---|
| NAM | 7 mg |
| DiSU | 2000 mg |
| Succinic acid | qs to pH 6.5 |
| Water | to 330 ml |

This Beverage (molar ratio choline:succinate:NAM is about 2:1:0,01), when administered orally to a subject daily, 330 ml per serving, one or more servings, is useful for enhancing of brain healthy functioning.

Beverage 7. The Beverage is prepared by mixing of NAM with DiSU in amounts as indicated below and dissolved in 330 ml of water to provide a Beverage.

Beverage 7

| Ingredient | Content, per serving |
|---|---|
| NAM | 37 mg |
| DiSU | 250 mg |
| Citric acid (or D-gluconic acid for e.g., Ex. 7-9) | qs to pH 6.5 |
| Water | to 330 ml |

This Beverage (molar ratio choline:succinate:NAM is 2:1:0.4), when administered orally to a subject daily, 330 ml per serving, one or more servings, is useful for improvement of brain energy metabolism in a subject, helping the subject to maintain high mental endurance and persistent feeling of well-being.

Example 2

Evaluation of the Effect of DiSU on Energy Metabolism in Ischemia Damaged Brain In Vivo Male rats received 10 mg/kg DiSU (n=8), 10 mg/kg disodium succinate (n=8), 10 mg/kg dipotassium succinate (n=8), 10 mg/kg choline chloride (n=8), or saline (control, n=23) for 7 days. Then global ischemia was induced in rats by cardiac arrest under anesthesia and whole-brain ATP levels were measured by 31P NMR in vivo for 15 min. Results are presented in Table 3 as mean±SEM ATP levels in the brain at $15^{th}$ min after ischemia onset, in percent to baseline (accepted for 100%).

TABLE 1

| | ATP, % |
|---|---|
| Saline (control) | 35.3 ± 3.0 |
| Disodium succinate | 34.3 ± 2.4 |
| Dipotassium succinate | 40.9 ± 9.0 |
| Choline chloride | 36.8 ± 5.0 |
| DiSU | 55.5 ± 4.8* |

*Differs significantly from saline ($p < 0.05$, t-test).

The data of Table 1 shows that DiSU protects the brain from ATP decline at global hypoxia as compared to the control, while DiSU constituents choline and succinate, taken individually and in the same doses, were not effective. Notably, DiSU protection of brain energy metabolism was significant while another succinate salt, disodium succinate, was not effective. Also another choline salt, choline chloride, was not effective in protection of brain energy metabolism. Thus, DiSU significantly differs from other choline and succinate salts in its capacity to protect brain energy metabolism in ischemic conditions. Notably, DiSU did not affect ATP levels in the brain under normoxia.

Example 3

Evaluation of the Effect of a Composition on the Production of ATP in Brain Cells In Vitro Materials and methods. Mixed primary cultures of cortical neurons and glial cells were prepared from mouse pups 1-3 days postpartum, as described by Vaarmann A. et al., 2010 (Cell Calcium 2010, 48(2-3):176-82). For measurements of ATP, the cells at 14-21 DIV were transfected for 24 h with the ATP sensing probe AT1.03 (as described in Imamura H et al., PNAS 2009, 106(37):15651-15656) using Lipofectamine 2000 according to the manufacturer's instructions. In experiments, cells were exposed to 50 μM DiSU, 20 μM NAM, nicotinic acid (niacin) (20 μM), composition of 50 μM DiSU and 20 μM NAM, composition of 50 μM DiSU and 20 μM nicotinic acid, or none (control) for about 5 min. Then, ATP levels in cells were measured using confocal microscopy. In another series of experiments, cells were exposed to reference compounds including sodium succinate (50 μM), choline bitartrate (100 μM), or compositions thereof and the ATP levels in cells have also been obtained for comparison. All data presented were obtained from at least 5 coverslips and 2-3 different cell preparations.

Results: Data are presented in Table 2 as mean of ATP levels in cells. Mean of ATP levels in non-treated cells (control) was accepted for 100%. Effects of the treatments on ATP levels in cells (ΔATP) were calculated by formula: ΔATP=ATPtreat−ATPcontrol, wherein ATPtreat is ATP level in treated cells and ATPcontrol is ATP levels in control cells.

TABLE 2

| Treatment | ATP, % | ΔATP, % |
|---|---|---|
| control | 100 | 0 |
| DiSU | 242* | +142 |
| Sodium succinate | 123 | +23 |
| NAM | 114 | +14 |
| Nicotinic acid | 101 | +1 |
| Choline bitartrate | 140 | "+40 |
| DiSU and NAM | 328*# | +228 |
| DiSU and nicotinic acid | 252*† | +152 |
| Sodium succinate and NAM | 142 | +42 |
| Sodium succinate and NAM and choline bitartrate" | 246*† | +146 |

*differs significantly from control ($p < 0.05$).
#differs significantly from DiSU ($p < 0.05$).
†differs significantly from control ($p < 0.05$).

Table 2 shows that treatment with the composition consisting of DiSU and NAM results in a significant synergistic increase in intracellular ATP levels by 228% compared to the control (p<0.05). The effect of the composition ΔATP=228% was 1.5-fold greater than sum of the effects ΔATP=142+14=156% of the individual components, DiSU and NAM, respectively. There is a significant difference between the effect ΔATP=228% of the composition and the effect ΔATP=142% of DiSU alone (p<0.05). Thus, the composition is synergistically effective for the improvement of ATP production in brain cells.

Treatment with the composition of DiSU and Nicotinic acid results in an increase in intracellular ATP levels by 152.0% compared to the control (p<0.05). There is no significant difference between the effect ΔATP=152% of the composition and the effect ΔATP=142% of DiSU alone (p>0.05). The sum of the individual effects ΔATP=142+1=143% of DiSU and Nicotinic acid is similar by value to the effect ΔATP=152% of the composition. Thus, the combined effect of the compounds of the composition on the production of ATP is non-synergistic. Despite NAM and nicotinic acid (niacin) generally being considered members of vitamin B3 family with similar biological capabilities, the presented data clearly show that their effects on the production of ATP in brain cells when they are combined with DiSU are different.

Treatment with the composition of sodium succinate and NAM and choline bitartrate results in a significant synergistic increase in intracellular ATP levels by 146% compared to the control (p<0.05). The effect of the composition ΔATP=146% was about 1.8-fold greater than sum of the effects ΔATP=23+14+40=77% of its individual components, sodium succinate, NAM, and choline bitartrate. Thus, the composition of sodium succinate, NAM, and choline bitartrate was also synergistically effective for the improvement of ATP production in brain cells.

The data indicates that the presence of choline anion in a composition comprising a succinate salt and NAM is important for the synergetic generation of ATP in mitochondria. There is a significant difference between the effect of the composition sodium succinate, NAM, and choline bitartrate (ΔATP=146%) and the effect of the composition "sodium succinate and NAM" (ΔATP=42%) (p<0.05). Thus, the composition comprising succinate anion, choline cation, and NAM is synergistically effective for the production of ATP in brain cells.

The choice of combination of succinate anion and choline cation is relevant to the scale of the synergetic effect of the composition. There is a significant difference between the DiSU and NAM composition and the sodium succinate, NAM, and choline bitartrate composition in their effects on ATP production in the brain cells (p<0.05). The composition including DiSU and NAM was about 1.6-fold more effective than sodium succinate, NAM, and choline bitartrate composition despite on the same molar concentrations of choline cation, succinate anion, and NAM in the compositions. This indicates that DiSU is a superior representative for the combination of choline anion and succinate cation.

Treatment individually with sodium succinate and NAM, or a composition thereof, results in a non-significant increase in intracellular ATP levels compared to the control (p>0.05), by 23%, 14%, or 42%, respectively. The sum of the individual effects ΔATP=23+14=37% of sodium succinate and NAM is similar by value and slightly smaller, compared to the effect of the composition, ΔATP=42%. Therefore, the composition of sodium succinate and NAM is not synergistically effective for the ATP production in the brain cells, which is in sharp contrast to the composition comprising succinate anion, NAM, and choline cation.

Accordingly, the results show that a composition including choline cation, succinate anion and NAM at the molar ratio of about 2:1:0.4 is effective for the enhancement of ATP production in the brain cells.

Example 4

Evaluation of the Effect of a Composition of the Production of NADH in Brain Cells In Vitro NADH is a donor of electrons for electron transport chain in mitochondria. The level of NADH in mitochondria is a balance between production of this molecule in the citric acid (TCA) cycle and consumption of it in complex I. Measurements of NADH in live cells (tissue) can be done using autofluorescence of NADH (excitation 360 nm, emission ~430 nm). However, the mitochondrial signal of NADH could not be separated from NADPH autofluorescence or from the cytosolic NADH signal.

Methods and Results

Mixed cultures of cortical neurons and glial cells were prepared as described, from mouse pups 1-3 days postpartum. Neurons were easily distinguishable from glia: they appeared phase bright, had smooth rounded somata and distinct processes, and positioned just above the focal plane of the glial layer. Cells were used at 14-21 DIV. Experiments were conducted in HBSS solution at the 37° C.

To estimate the mitochondrial pool of NADH, maximal activation of mitochondrial respiration is induced by uncoupler FCCP (mitochondrial NADH is taken 0) followed by inhibition of respiration by NaCN (NADH is maximal due to inhibition of consumption). This set up provides evaluation of several characteristics: the rate of NADH production in TCA cycle (recovery of the NADH signal after NaCN), total mitochondrial pool and redox index.

Application of sodium succinate (50 μM) to primary neurons and astrocytes induced fast and significant decrease of the mitochondrial NADH level which corresponds to activation of complex I-related respiration (n=156 cells, N=3 experiments). This is a typical effect of the addition of succinate which needs to be compensated by the following NADH production. DiSU in comparison to sodium succinate induced only slight initial decrease in mitochondrial NADH followed by a slow steady increase in NADH autofluorescence (to 123±6% of control after 20 min of incubation). There was not detected a noticeable increase in NADH autofluorescence after 20 min of incubation with sodium succinate.

Adding a combination of NAM (20 μM) and DiSU (50 μM) (the molar ratio choline:succinate:NAM was about 2:1:0.4) not only reduced initial drop in NADH, but significantly increased NADH autofluorescence detected in 20 min following the initial drop (161±11% of control; n=132; N=3 experiments). Application of NAM (20 μM) alone in short term (15-20 min) induced only moderate increase (to 116±8% of control) in mitochondrial NADH pool (N=3; n=68 cells).

Accordingly, a combination of DiSU and NAM has a significantly higher effect on the generation of NADH in brain mitochondria than the single compounds of the composition, and that the effect of the individual compounds is synergistic.

Based on the above results, we conclude that a composition including DiSU and NAM is effective for the generation of NADH in the brain cells.

Example 5

Evaluation of the Effect of Intake of a Beverage Comprising DiSU and NAM on the Level of Phosphocreatine in Human Brain In Vivo ATP is strongly buffered in the brain by conversion via creatine kinase-catalyzed reaction to phosphocreatine (pCr), the phosphorylated analogue of the guanidino amino acid creatine. ATP can be resynthesized from phosphocreatine 12 times faster than via oxidative phosphorylation and more than 70 times faster than de novo pathways. Phosphocreatine (pCr) is a high energy substrate that serve as a reserve ("temporal energy buffer") in the brain to recycle adenosine triphosphate (ATP), the direct energy source for energy-consuming reactions in the cell.

Methods

A volunteer (57 years old healthy female subject) received a Beverage containing 500 mg of DiSU and 188 mg NAM (the molar ratio choline:succinate:NAM is about 2:1:1) in 100 ml of water, once-a-day for seven consecutive days. The volunteer has been maintaining the normal diet and did not receive any other food supplements during the trail. Whole-brain levels of PCr and ATP were obtained using the 31P magnetic resonance spectroscopy (31P MRS). 31P MRS at 3 Tesla (3T) at day 0 (just before the Beverage intake), day 7 and day 16 (following the Beverage intake). The ratio pCr-to-γATP signals (pCr/ATP) in 31P MRS spectra was used as a measure of the pCr levels in the brain. At every session, 31P MRS spectra were recorded in three replicates (n=3); signals related to pCr, ATP were evaluated and the pCr-to-ATP ratio were calculated. Effect of the Beverage intake on pCr/ATP ratios (ΔpCr/ATP) in the brain was calculated by formula: ΔpCr/ATP=100% (mean pCr/ATP-day7/16−mean pCr/ATPday0)×100%/mean pCr/AT day0. *Indicates significant between-groups mean differences in t-Student test (p<0.05).

Results

The results of the 31P MRS measurements are presented in Table 3. The data are presented as mean±sem (n=3) for pCr, ATP, pCr/ATP, and ΔpCr/ATP.

TABLE 3

| Day of $^{31}$P MRS recording | pCr/ATP | ΔpCr/ATP, % |
|---|---|---|
| Day 0 | 1.138 ± 0.015 | |
| Day 7 | 1.220 ± 0.022* | +7 |
| Day 16 | 1.288 ± 0.015* | +13 |

*Differs significantly from a value at day 0 ($p < 0.05$).

As it can be seen from the data presented in Table 3, intake of the Beverage containing DiSU and NAM, where the molar ratio choline:succinate:NAM is about 2:1:1, results in a significant increase in the level of brain phosphocreatine (PCr) after 7 days of the consumption that continues to increase by the 16th day of consumption, by 7% and 13% compared to baseline value (at day 0), respectively. No significant changes in brain ATP levels to the baseline (day 0) were recorded neither at day 7 (p=0.48) or day 16 (p=0.57), indicating that a steady-state ATP levels in the brain are stable.

Accordingly, we conclude that the composition is effective in supporting the brain energy metabolism and energy reserves necessary for complex mental activity in any human individual, and in particular in an aging individual where mental activity is decreased.

Example 6

Evaluation of the Intake of a Beverage Comprising DiSU and NAM: Human Trial Study Design A total of 20 male and female healthy adults (21-63 years old) were recruited to participate in the study. The participants were randomized into 2 groups, each of 10 subjects. First group was receiving Beverage A (see Table 4 below). Second group was receiving Beverage B (placebo product).

The placebo and treatment products were bottled Beverages in the 500 ml dosage container.

TABLE 4

| | |
|---|---|
| Beverage A (identical to Beverage 4 described above) | A solution of 560 mg DiSU and 210 mg NAM in water |
| Beverage B | Water |

The study questionnaire was distributed to participants and filled out (see below). Participants also received a supply of the study Beverages in doses, one dose per day for continued consumption for the period of 12 weeks. Participants were instructed to consume the products during the day before 18:00 and reminded to avoid consuming more than 250 mg caffeine and less than 2.5 g taurine per day during the study period. The participants were instructed to fill out the questionnaire (1) in the end of the twelfth week following the start of the consumption of the Beverage. In the end of the study (end of the twelfth week) the participants delivered the questionnaire and, additionally, they were interviewed regarding their general experience of the Beverage (distributed and filled the Beverage evaluation questionnaire (2) (see below)).

Results of the Study

The symptom evaluation (questionnaire 1).

| | | Before the study | | After the study | |
|---|---|---|---|---|---|
| Symptom | Assessment | Group A | Group B | Group A | Group B |
| Mood swings | Often[1)] | 3 | 1 | 0 | 1 |
| | Seldom[2)] | 5 | 6 | 8 | 6 |
| | Never[3)] | 2 | 3 | 2 | 3 |
| Fatigue | Often | 5 | 6 | 0 | 5 |
| | Seldom | 3 | 2 | 8 | 3 |
| | Never | 2 | 2 | 2 | 2 |
| Stress | Often | 4 | 2 | 0 | 2 |
| | Seldom | 4 | 7 | 8 | 7 |
| | Never | 2 | 1 | 2 | 1 |
| Insomnia | Often | 3 | 3 | 1 | 4 |
| | Seldom | 5 | 6 | 7 | 5 |
| | Never | 2 | 1 | 2 | 1 |
| Loss of Focus | Often | 4 | 5 | 1 | 4 |
| | Seldom | 6 | 5 | 6 | 7 |
| | Never | 0 | 0 | 3 | 0 |
| Bad Mood | Often | 2 | 1 | 0 | 0 |
| | Seldom | 5 | 5 | 3 | 7 |
| | Never | 3 | 4 | 7 | 3 |
| Seasonal Affective Disorder | Yes | 2 | 4 | 0 | 4 |
| | No | 8 | 6 | 10 | 6 |

*The study was run during 12 weeks through November, December, and January.
[1)]Often = daily or several times a day and without an obviously serious reason
[2)]Seldom = sometimes and due to a reason, reason being not obvious
[3)]Never = time to time and only due to an obvious reason The Beverage experience evaluation (questionnaire 2).

| Parameter | Assessment | Group A | Group B |
|---|---|---|---|
| Taste | Pleasant | 4 | 5 |
| | Neutral | 6 | 5 |
| | Unpleasant | 0 | 0 |
| General Experience | Good (satisfaction with the results of consumption, wishing to continue) | 8 | 3 |
| | Neutral (no noticeable effects, may consider continuing) | 2 | 7 |
| | Bad (there are some negative effects of the intake; not wishing to continue) | 0 | 0 |

From the data of questionnaire 1 it can be concluded that the physical condition of subjects of Group A did in general improve as they experienced a change from “worse to better” in all of the assessed symptoms. At the same time, not many changes were observed in the symptoms during the trial in the subjects of group B. Most of the symptoms, if not all, are generally associated with lack of energy in the brain or unbalance in the brain energy metabolism. It can therefore be concluded that implementations of the composition are useful to maintain a healthy level of, or to enhance, the brain energy metabolism in the general public. Indeed, the general public is exposed daily to a vast amount of socio-environmental stimuli which demand mental energy to deal with, leading to exhaustion of the brain energy reserves, and consequently, to development of the above symptoms.

Example 7

Evaluation of the Effect of Compositions of the Invention on Cellular Energetics and Mitophagy in Primary Cultures of Myocytes

Materials and Methods

Primary Skeletal Muscle Cell culture. Primary myotube cells were obtained from postnatal day 0-2 (P0-P2) rat pups which were sacrificed by decapitation. Briefly, the rats were immersed in 70% ethanol and the hind-limbs removed under a dissection microscope, in dissection solution containing Dulbecco’s Phosphate Buffered Saline (PBS) with penicillin streptomycin (5000 units/ml) and Amphotericin B (2.5 mg/L). The tissues were then digested in 0.2% collagenase solution at 37° C. for 30-40 minutes.

The reaction was stopped by adding 2-3 ml fetal bovine serum (FBS), and the tissue suspension was centrifuged at 2010 rpm (700 g) for 10 minutes. The cell pellet was resuspended in pre-warmed growth medium, Dulbecco’s modified Eagle’s medium (DMEM), containing 20% FBS, 100 i.u./ml penicillin and 200 i.u./ml streptomycin], and plated on 22 mm coverslips that were pre-coated with 0.2% gelatin for 1 hour at 37° C. Cells were then cultured in a humidified CO2 incubator (5% CO2 in air) at 37° C. After 2 or 3 days, the medium was changed to a low-serum medium (DMEM containing 10% FBS without antibiotics), and was subsequently renewed every 3 or 4 days. All experiments were performed in vitro between days 2 and 11 in culture when spindle-shaped myoblasts had proliferated and aligned themselves for fusion (~70% confluency).

Effect of compositions of the invention on capacity of primary myocyte (myotubes) mitochondria to produced “energy” molecules ATP, NAD and FAD was assessed in resting cells and activated cells in the cellular model of exercise (myotubes contractions are induced by different caffeine concentrations, as described below).

In particular, the effect of acute application of the compounds (i.e. di-choline succinate (DiSU) and nicotinamide (NAM) and a combination thereof) on mitochondrial membrane potential, level of mitochondrial NADH and FAD, and intracellular ATP was studied on resting myotubes using a 24- and 48-hours incubation of the myotubes with the compounds.

Myotubes activated by 1 mM caffeine to induce singe calcium peaks and myotube contractions to simulate 'physiological' level of myotube activity resembling the activity of exercise, 5 mM caffeine to stimulate a near maximal [Ca2+]c signal and fast contractions of myotubes, and 10 mM caffeine to cause potentially damaging [Ca2+]c overload, were used as an "exercise model". The cell cultures are incubated with the compounds to evaluate the effect on the level of production of ATP, NAD, FAD and mitochondrial membrane potential during exercise.

Confocal Microscopy. Confocal images were obtained using an inverted Zeiss 710 uv-vis CLSM equipped with a META detection system and a 40× oil immersion objective. The 488 nm Argon laser line was used to excite fluo-4, MagFluo-4 fluorescence, which were all measured using a bandpass filter of 505-550 nm. Illumination intensity was kept to a minimum (at 0.1-0.2% of laser output) to avoid phototoxicity and the pinhole set to give an optical slice of ~2 μm.

NADH and its oxidized form NAD act as hydrogen carriers at the site of the electron transport chain during mitochondrial respiration. The fluorescent properties of NADH make it a valuable fluorescent indicator of the mitochondrial metabolic state. NADH autofluorescence was excited at 351 and measured at 375-470 nm.

Tetramethyl rhodamine methyl ester (TMRM) was used to study the changes of the mitochondrial membrane potential ($\Delta\psi_m$). Cells were loaded with 25 nM TMRM for 40 min until a steady state was achieved. TMRM fluorescence was excited at 543 nm (HeNe laser), and emission was measured at >560 nm. The positively charged lipophilic compound is sequestered into the mitochondria by virtue of their negative potential compared to the cytosol. Therefore, the changes in potential are reflected by changes in fluorescence intensity within the mitochondria which is measured after thresholding out the background signal from the cytosol to give a mean value per pixel within the mitochondrial population of a cell. It is important to emphasize that this measure is completely independent of mitochondrial mass or number in a cell.

Evaluation of the mitochondrial FAD level was done as described above for NADH.

All presented results are obtained from at least 5 coverslips and 2-3 different cell preparations.

Results

Evaluation of the Mitochondrial Membrane Potential (Δψm)

Treatment of primary myotube cultures loaded with TMRM with (1) di-choline succinate (DiSU, 50 μM), (2) nicotinamide (NAM; 20 μM) or (3) simultaneously with 50 μM DiSU and 20 μM NAM (ratio choline:succinate:nicotinamode=2:1:0.4) induced a increase in TMRM fluorescence compared to control. Subsequent application of the 1 μM FCCP induce complete mitochondrial depolarisation and decrease the TMRM signal confirming ability of the compounds to increase mitochondrial membrane potential. The mixture of DiSU and NAM (treatment 3) had the highest effect—21±2% (p<0.05; n=67 myotubes), compared to DiSU (treatment 1) and NAM (treatment 2).

Evaluation of the Mitochondrial NADH Pool

NADH is produced in the Krebs cycle inside of mitochondria. It is used as a donor of electrons and substrate for the mitochondrial complex I. NADH is a fluorescent compound and this allows to measure its level in the mitochondria. However, NADH fluorescence cannot be distinguished from the fluorescent signal deriving from NADPH. To separate these two fluorescent signals, mitochondrial activators and inhibitors can be utilized.

Accordingly, to measure the resting level of NADH autofluorescence, it was generated the "redox index," a ratio of the maximally oxidized (response to 1 μM FCCP, a potent uncoupler of mitochondrial oxidative phosphorylation, —mitochondria respiring maximally with minimal level of NADH in mitochondria) and maximally reduced (response to 1 mM NaCN, a potent inducer of decrease in the mitochondrial membrane potential—both respiration and consumption of the NADH in mitochondria is blocked, which leads to the maximal values of NADH as shown in the autofluorescence graphs of NADH depicted in FIG. 1A.

Figure 1B:
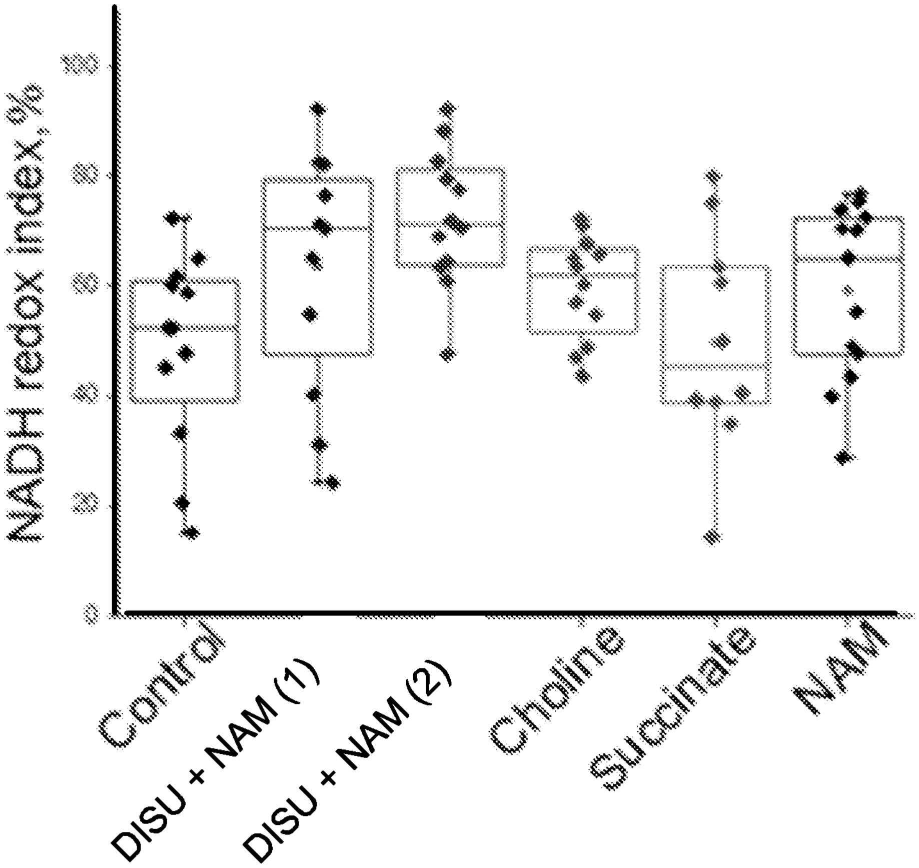
FIG. 1B shows NADH redox index for treatment of myotube culture with compositions of different blends of DiSU vs individual compounds and vs a control.
Figure 1C:
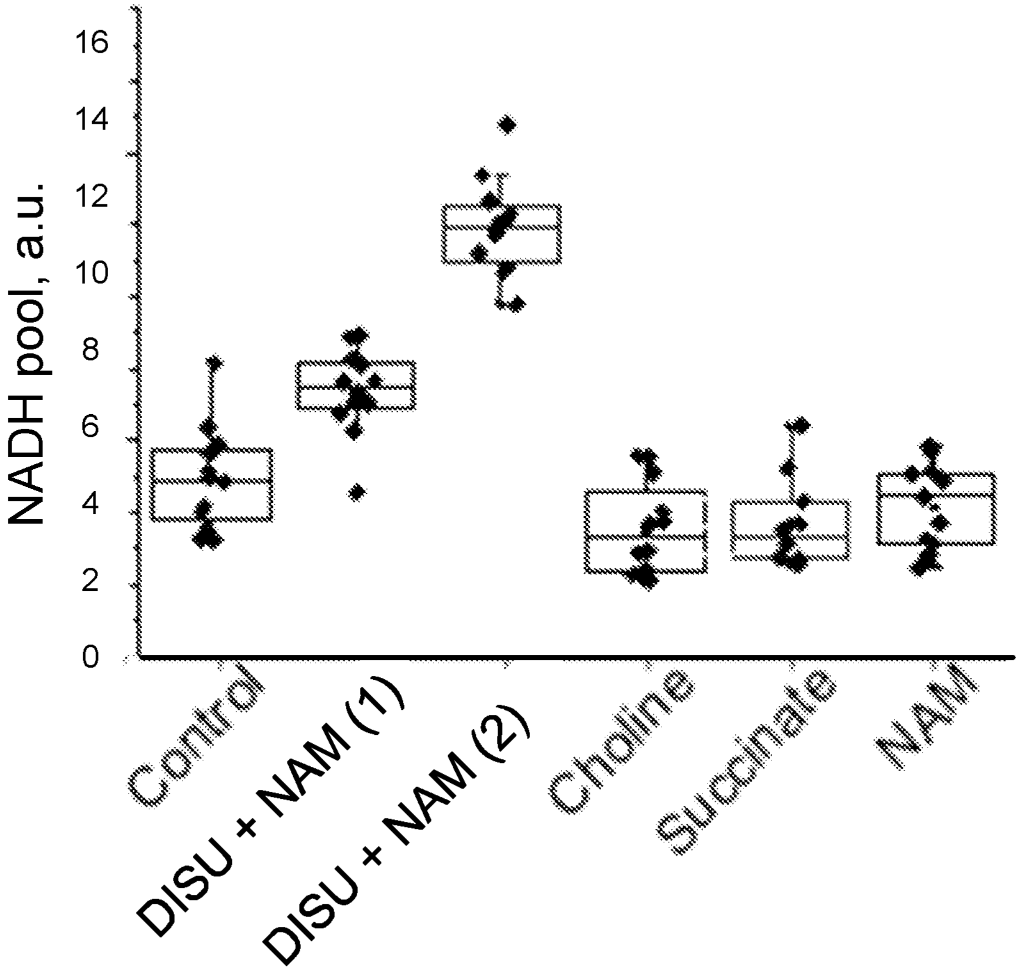
FIG. 1C shows significant increases in the mitochondrial pool of NADH for different blends of DiSU and NAM vs individual compounds and vs a control.

Treatment of myotube cultures with two different blends DiSU+NAM (blend 1: 100 μM DiSU+40 μM NAM; blend 2: 50 μM DiSU+20 μM NAM; the molar ration choline: succinate:NAM=2:1:0.4), or with single compounds of the blends, i.e. choline (100 succinate (50 μM), NAM (50 μM) did not induce significant changes in the redox index (which corresponds to NADH-dependent mitochondrial respiration as seen in the results shown in FIG. 1B. However, both blends of DiSU and NAM, but not the individual components, significantly increased the mitochondrial pool of NADH (measured as a Δ between FCCP and NaCN NADH autofluorescence as seen in the experimental results shown in FIG. 1C.

Evaluation of the FAD Level

FADH is essential for mitochondrial complex II and also a biological marker of the functionality of mitochondria.

FAD++ is fluorescent and the mitochondrial level of FAD+++ was measured based on evaluation of its autofluorescence (in the same way as described above for NADH) (FIG. 3A). Treatment of myotubes with a blend of DiSU and NAM (50 μM DiSU+20 μM NAM; the molar ration choline: succinate:NAM=2:1:0.4) resulted in an increase of the mitochondrial pool of FAD++ (FIG. 3B).

Evaluation of the Overall Energy Capacity of the Activated Myotubes

Figure 4:
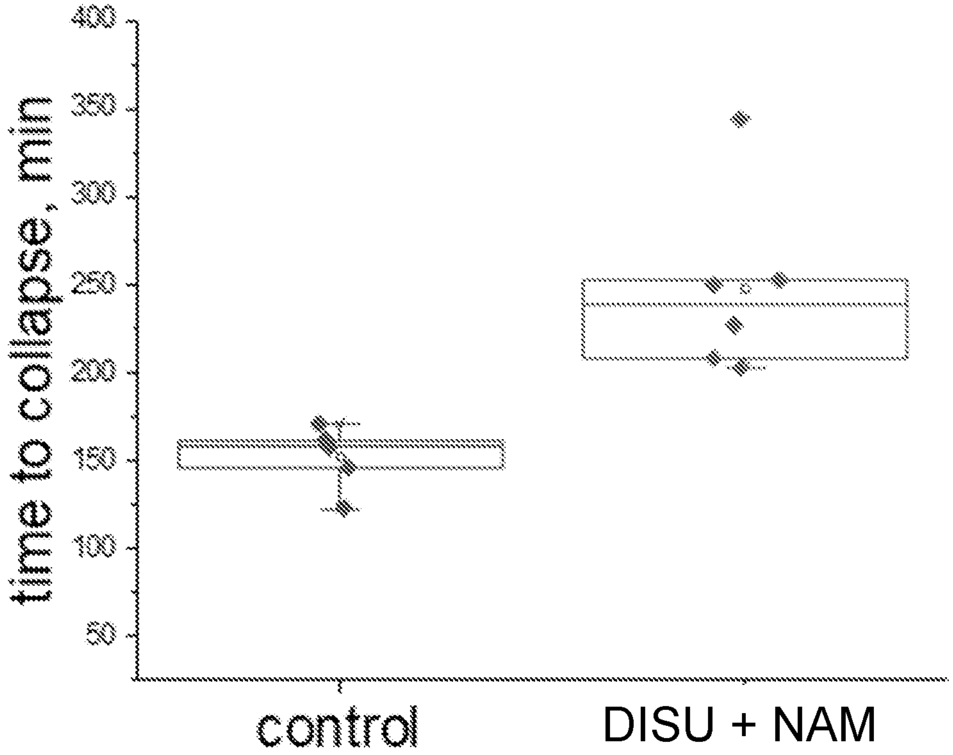
FIG. 4 shows a box plot of representative results of an evaluation of energetic capability of primary myotubes stimulated to contract with caffeine with a blend of DiSU and NAM versus a control.

The energy capacity of the cell is defined as the time between cessation of ATP production and the time of energetic collapse due to total ATP depletion and inability to maintain calcium homeostasis. Live-cell imaging of the fluorescent probe MagFura-2 was used to assess the energy capacity primary myotubes. Mg2+ is released from MgATP upon the hydrolysis of ATP, so the measurement of cellular free magnesium ([Mg2+]c) using the Mg2+-sensitive fluorescent probe MagFura-2 can be used as an indication of ATP consumption (Leyssens et al., (1996) *J Physiol.* 496, 111-128). Application of inhibitors of glycolysis and/or oxidative phosphorylation blocks the ATP production in cells, which eventually leads to ATP depletion and subsequent Mg2+ release and an increase in Mag-Fura fluorescence (FIG. 4). To estimate the overall ATP consumption, inhibitors of glycolysis (iodoacetic acid, 20 μm) and F1F0-ATP synthase (oligomycin, 2 μg/ml) were applied simultaneously. Additionally, the cultures were treated with 1 mM of caffeine to induce calcium dependent myotubes contractions to mimic muscle exercise, which leads to an increased consumption of ATP (FIG. 4).

It is found that treatment of primary myotubes with a blend of 50 μM DiSU and 20 μM NAM; the molar ration choline:succinate:NAM=2:1:0.4, significantly increases the time of contraction of myotubes to myotube collapse (from 147±7 to 238±9 min). This surprising finding strongly suggests that simultaneous treatment of myotubes with DiSU and NAM increases the myotube energy capacity and thereby enhancing the capability of the muscle cells to sustain contraction for a longer period of time.

Evaluation of Autophagy

Figures 2A, 2B:
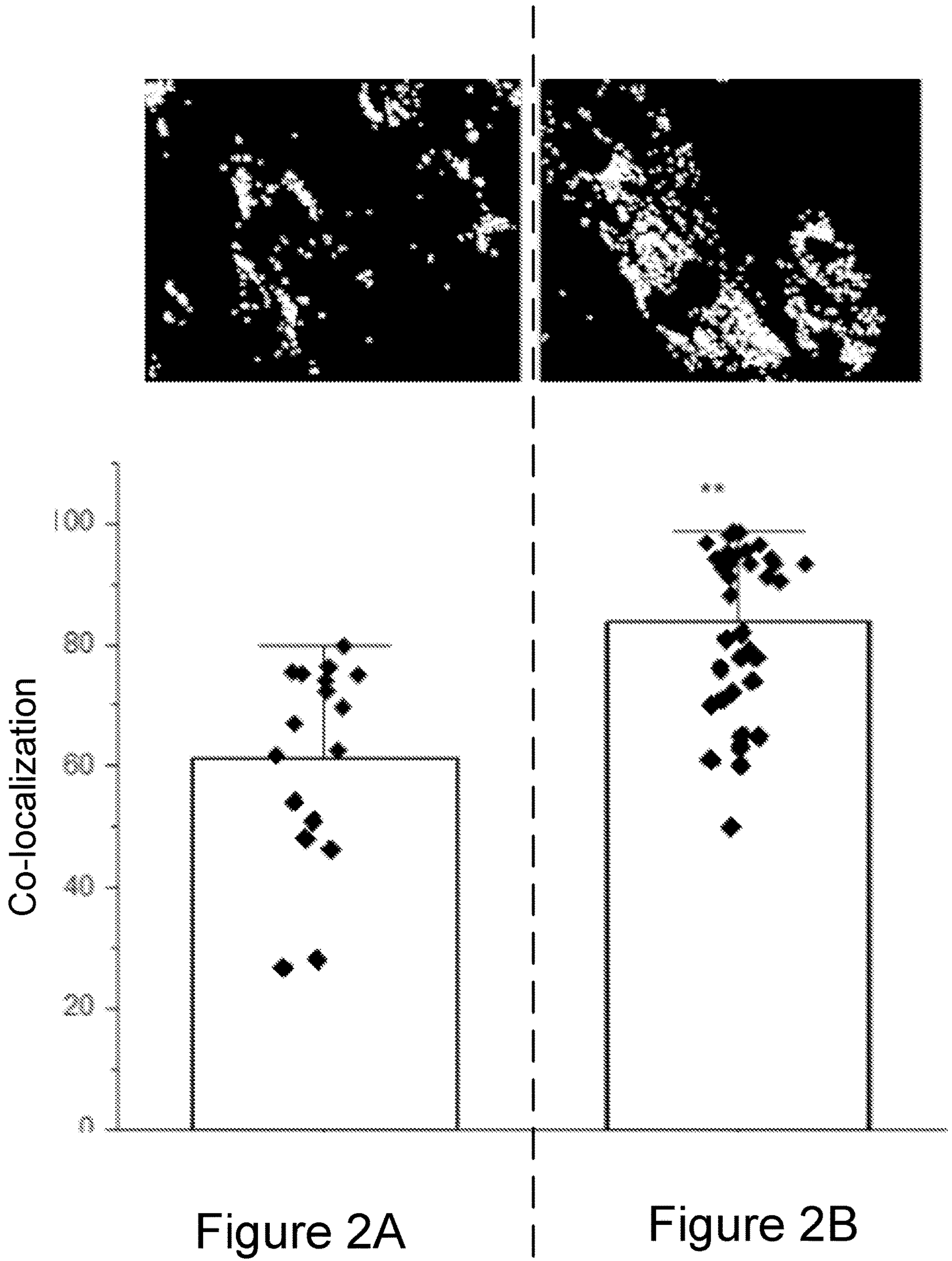
FIG. 2A shows minimal autophagy in primary myotubes treated with a control.
FIG. 2B show synergistically increased autophagy in primary myotubes treated with DiSU and a synergistically effective amount of NAM.

Mitophagy induced by treatments of primary myotubes either with a blend of DiSU and NAM (50 μM DiSU+20 μM NAM; the molar ration choline:succinate:NAM=2:1:0.4) or single components of the blend (DiSU, NAM, choline, succinate (all compounds are used in the molar amounts corresponding to the molar amounts of the compounds in the blend) was evaluated by analyzing the level of cellular co-localization of mitochondria (labelled with MitoTracker Green (green color)) and lysosomes (labeled with LysoTracker Red, red color) using confocal microscopy. Both DiSU and the blend of DiSU and NAM, but not NAM, choline bitartrate, or succinate di-sodium salt, were potent to significantly increase autophagy in the treated cultures of primary myotubes. FIG. 2A demonstrate the results of control (non-treated) cells vs FIG. 2B which shows the results of cell treatment with the synergistic blend of DiSU and NAM.

Summary of Evaluation of the Production of ATP, NAD and FAD

Table 5 below summarizes results on the production of ATP, NADH and FAD in resting myocytes in response to treatment with different formulations of choline, succinate and nicotinamide or nicotinic acid. The levels of ATP, NADH and FAD in treated cells were normalized to the levels in control cells

TABLE 5

| Treatment of resting myocytes | ATP | NADH | FAD |
|---|---|---|---|
| Control (no treatment) | – | – | – |
| DiSU | ++ | ++ | + |
| Succinate* | + | – | – |
| NAM | + | + | – |
| Nicotinic acid | – | – | – |
| Choline** | + | – | – |
| DiSU + NAM | ++++++ | +++++ | +++++ |
| DiSU and Nicotinic acid | + | – | – |
| Succinate* and NAM | – | – | – |
| Choline** + Succinate + NAM | +++ | ++ | ++ |

*Sodium succinate (salt);
**Choline bitartrate

In Table 5, in all combined treatments with choline, succinate and NAM/nicotinic acid, the molar ratio choline: succinate:NAM/nicotinic acid is 2:1:0.4.

Table 6 below summarizes results on the production of ATP, NADH and FAD in myocytes activated with different concentrations of caffeine in response to treatment with different formulations of choline, succinate and nicotinamide or nicotinic acid. The levels of ATP, NADH and FAD in treated cells were normalized to the levels in control cells.

TABLE 6

| | 1 mM caffeine | | | 5 mM caffeine | | | 10 mM caffeine | | |
|---|---|---|---|---|---|---|---|---|---|
| Treatment | ATP | NADH | FAD | ATP | NADH | FAD | ATP | NADH | FAD |
| Control (no treatment) | – | – | – | – | – | | – | – | – |
| DiSU | ++ | ++ | + | ++ | + | + | + | + | + |
| Succinate* | – | – | – | – | – | – | – | – | – |
| NAM | + | – | – | – | – | – | – | – | – |
| Nicotinic acid | – | – | – | – | – | – | – | – | – |
| Choline** | – | – | – | – | – | – | – | – | – |
| DiSU + NAM | +++++ | ++++ | ++++ | ++++ | ++++ | ++++ | +++ | +++ | ++ |
| DiSU + Nicotinic acid | + | + | – | – | + | + | + | – | – |
| Succinate* + NAM | + | – | – | – | – | – | – | – | – |
| Choline** + Succinate* + NAM | +++ | ++ | ++ | ++ | + | + | ++ | + | + |

*Sodium succinate (salt);
**Choline bitartrate

In Table 6, in all combined treatments with choline, succinate and NAM/nicotinic acid, the molar ratio choline: succinate:NAM/nicotinic acid is 2:1:0.4.

The results presented in Table 5 and Table 6 show that treatment of resting myocytes with the composition consisting of DiSU and NAM (molar ratio choline:succinate: NAM=2:1:0.4) results in a significant increase in intracellular levels of both ATP, NADH and FAD compared to the control ($p<0.05$). The effect of the composition was approximately 1.5-fold greater than sum of the effects of the individual components, DiSU and NAM, respectively. This indicates that the compounds of the composition of the invention works in synergy improving production of ATP, NADH and FAD production in resting myocytes; treatment of activated myocytes with the composition consisting of DiSU and NAM (molar ratio choline:succinate:NAM=2:1:0.4) results in a significant increase in intracellular levels of both ATP, NADH and FAD compared to the control ($p<0.05$) both, in 1 mM, 5 mM and 10 mM caffeine activated cultures. Compared to results of treatment with the single compounds of the composition, the effect is synergetic.

Accordingly, compositions of the invention essentially consisting of choline cation, succinate anion and NAM in the molar ratio about 2:1:04 are effective for the enhancement of production of ATP, NADH and FAD in both resting and activated myocytes in vitro.

According to the invention, compositions where the molar ratio choline:succinate:NAM is within the range of 0.5-3:3-0.5:0.01-10 are effective for enhancing the generation of energy molecules NAD, FAD and ATP in mitochondria and enhancing autophagy in primary cultures of muscle cells. Therefore, the results presented in Tables 1 and 2 are representative and not limiting the scope of the invention to compositions with the molar ratio choline:succinate:NAM of 2:1:0.4.

Example 8. Study of Skeletal Muscle Function and Endurance Performance in Athletes Brief Description of the Study A randomized, double-blind, placebo-controlled study enrolling at least 36 (18 Elite and 18 Sub-Elite trained endurance male runners. 18 placebo and 18 Beverage 3 are given as a daily oral dose for 4-weeks.

Study Details:

| | |
|---|---|
| Allocation: | Randomized |
| Intervention Model: | Parallel Assignment |
| Masking: | Triple (Participant, Investigator, Outcomes Assessor) |
| Primary Purpose: | Testing of the effect of Beverage 3 |
| Active Comparator: | Dietary Supplement: Beverage 3 (Example 1) |
| | 1 dose of Beverage 3 to be taken daily |
| Placebo Comparator: | Dietary Supplement: Beverage containing only excipients. |
| | 1 dose of Placebo to be taken daily |

Eligibility Criteria

Inclusion Criteria:

Trained elite and sub-elite male runners, age between 18-40 years

Participants will be running >100 km/week

Elite participants—required to have a 3,000 m running personal best time below 9:00 (mm:ss), and/or a VO2max result greater than 65 ml·kg-1·min-1

The sub-elite cohort—required to have a 3,000 m running personal best faster than 10:00 min and/or a VO2max >60 ml·kg-1·min-1

Exclusion Criteria:

Subjects with diagnosed medical conditions involving thyroid function or other chronic disturbances of metabolic rate Subjects who are unable to complete the training or testing protocols Outcome Measures (Time Frame: 4 Weeks)

Primary Outcome Measures:

Change in plasma levels over time of creatine kinase (CK)

Change in race performance time during a 3000 m track race in elite runners

Secondary Outcome Measures:

Change from baseline in aerobic capacity (VO2max)

Change from baseline in running economy via indirect calorimetry

Change from baseline in lean body mass via Dual-energy X-ray Absorptiometry (DXA)

Change from baseline in body fat mass via Dual-energy X-ray Absorptiometry (DXA)

Change from baseline in Resting Metabolic Rate (RMR)

Change from baseline in maximal muscle strength during 1-repetition maximum leg press Change in iron absorption and hemoglobin mass via determination of carboxyhaemoglobin (percent HbCO) (sub-elite runners only)

Change in acylcarnitines levels via metabolomics in plasma change in mitochondrial function via respirometry in muscle biopsies (sub-elite runners only)

change in mitochondrial gene expression via RNA-seq in muscle biopsies (sub-elite runners only)

change in plasma levels of Urolithin A change in plasma levels of inflammatory marker CRP

Example 9. Study of Bioenergetics and Muscle Function Improvement in Elderly Skeletal Muscle Summary:

A randomized, double-blind, single-center, placebo-controlled trial enrolling 50-60 healthy elderly subjects (33 placebo and 33 Beverage 1 administration) who are ≥65 and ≤90 years of age with evidence of low mitochondrial function. Beverage 1 or Placebo are orally administered for 4 months.

Study Details:

| | |
|---|---|
| Allocation: | Randomized |
| Intervention Model: | Parallel Assignment |
| Masking: | Triple (Participant, Investigator, Outcomes Assessor) |
| Primary Purpose: | Testing the effect of Beverage 1 |
| Active Comparator: | Dietary Supplement: Beverage 1 (Example 1) 1 dose of Beverage 1 to be taken daily. |
| Placebo Comparator: | Dietary Supplement: Placebo Beverage (excipients containing Beverage) |
| | 1 dose of Placebo Beverage to be taken daily |

Eligibility Criteria:

Adult human volunteers of all sexes ≥65 and ≤90 years of age;

Capable of walking 6 minute walk distance of <550 meters

Have ATP max <1 mM/sec (in the hand FDI muscle);

Exclusion Criteria:

Subjects who have significant disease(s) or condition(s) which, in the opinion of the investigator, may put the subject at risk because of their participation in the trial or may influence either the results of the trial or the subject's ability to participate in the trial.

Hospitalization within 3 months for major atherosclerotic events (defined as combined incidence of myocardial infarction, urgent target-vessel revascularization, coronary bypass surgery and stroke) and for any hospitalization within 2 months.

Have any metal implants in the right limbs, including non-MRI compatible metal stents, titanium pins/markers, etc.

Have an implanted cardiac pacemaker or other implanted non-MRI compatible cardiac device.

Chronic, uncontrolled hypertension as judged by the Investigator (i.e., Baseline SBP >150 mm Hg, DBP >90 mm Hg) or a SBP >150 mm Hg or DBP >95 mm Hg at the time of screening or baseline. If the initial BP reading is above these values, the reading may be repeated one time within 20 minutes of the initial reading.

Body mass index <18 or >32 kg/m2

Severe chronic kidney disease requiring treatment with hemodialysis or peritoneal dialysis.

Additional laboratory abnormalities determined as clinically significant by the Investigator.

Clinically significant abnormalities on physical examination (as judged by the Investigator)

Clinically significant and chronic uncontrolled renal, hepatic, pulmonary, endocrine, neurologic disorders, bone, or gastrointestinal system dysfunction History of Seizures or Epilepsy History of serious mental illness as judged by the Investigator Oral temperature >37.5° C. at the time of the physical Suspicion, or recent history, of alcohol or substance abuse or tobacco use Subjects who in the opinion of the Investigator have a clinically significant abnormal 12-lead ECG during the screening period. Presence of atrial fibrillation, varying degrees of AV block, existence of a left bundle branch block, or evidence of previous myocardial infarction.

Subjects who are either unwilling to agree to refrain from using or are found to be using supplementary antioxidant vitamins (e.g., Coenzyme Q10, resveratrol, L-carnitine) from 7 days prior to dosing and throughout the treatment period Subjects who are either unwilling to agree to refrain from using or are found to be using the following dietary restrictions (pomegranate juice, walnuts, pecans, strawberry, raspberry blackberry) from 7 days prior to dosing and throughout the treatment period Are currently enrolled in a clinical trial involving an investigational product or non-approved use of a drug or device or concurrently enrolled in any other type of medical research judged not to be scientifically or medically compatible with this study Have participated, within the last 30 days from a clinical trial involving an investigational product. If the previous investigational product has a long half life, 3 months or 5 half-lives (whichever is longer) should have passed Primary Outcome Measures: (Time Frame: 4 Months)

Change in 6 minute walking distance (6MWD) at the end of study intervention compared to baseline.

Percent change from baseline in ATP max (maximal ATP synthesis rate) in hand skeletal muscle (via Magnetic Resonance Spectroscopy).

Secondary Outcome Measures (Time Frame: 4 Months):

Percent change from baseline in contraction number during a hand muscle fatigue test.

Percent change from baseline in ATP max (maximum ATP synthesis rate) in leg skeletal muscle (via MRS).

Percent change from baseline in contraction number during a leg muscle fatigue test.

Change in Short Physical Performance Battery (SPPB) scores at the end of study intervention compared to baseline.

Change in exercise tolerance compared to baseline (via cycle ergometry)

Change in hand grip strength at the end of study intervention compared to baseline.

Change in leg muscle strength (1-RM and 10-RM) at the end of study intervention compared to baseline.

Change in muscle size (cross-sectional area of the muscles) at the end of study intervention compared to baseline.

Change in mitochondrial function on muscle biopsy samples at the end of study intervention compared to baseline (via respirometry)

Effect of Beverage 1 on mitochondrial gene and protein expression in muscle tissue.

Effect of Beverage 1 on plasma acylcarnitines.

Effect of Beverage 1 on quality of life questionnaire (SF36)

Change from baseline in plasma lipid profile.

Change from baseline in plasma for circulating biomarkers (myostatin, follistatin)

FIGS. 2A-2B show representative results of the evaluation of autophagy in primary cultures of myotubes treated with a blend of DiSU and NAM (50 μM DiSU and 20 μM NAM; the molar ratio choline:succinate:nicotinamide is 2:1:0.4) evaluated as the level of co-localization of mitochondria and lysosomes. The upper panels show confocal images of cells loaded with two dyes MitoTracker Green (labeling mitochondria) and LysoTracker Red (labeling lysosomes); the lower panel: quotative evaluation of co-localization of mitochondria and lysosomes in cells. The cells were incubated in the absence (control, upper panel 2A) or in the presence of 50 μM DiSU and 20 μM NAM (treated cells, upper panel 2B). Values are presented as mean±SD. **P<0.001. Independent experiments (n) are indicated as dots in the scatter plot.

Figure 3A:
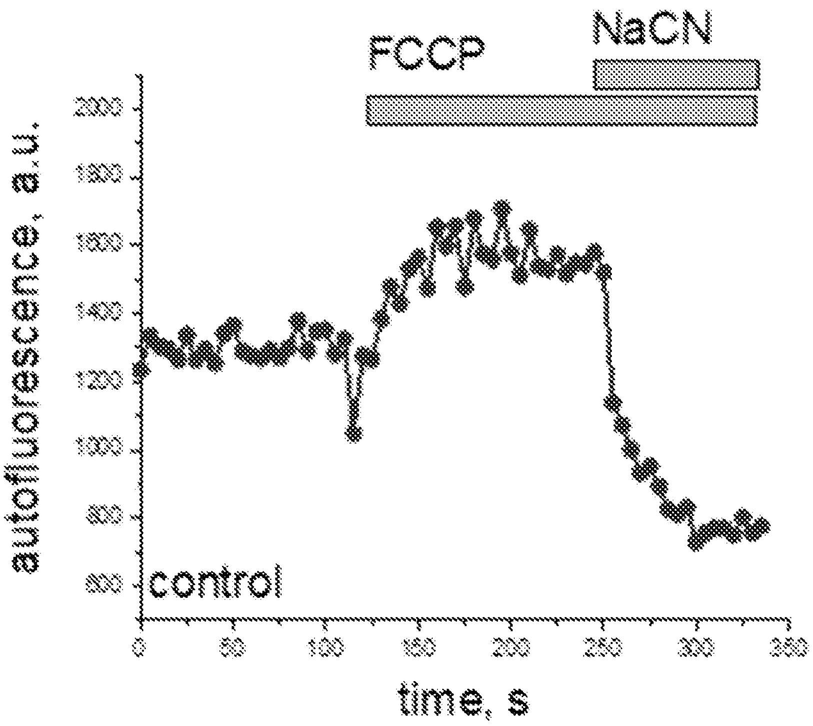
FIG. 3A shows a graph of representative results of the evaluation of treatment of cultures of primary myotubes with a blend of DiSU and NAM versus a control.
Figure 3B:
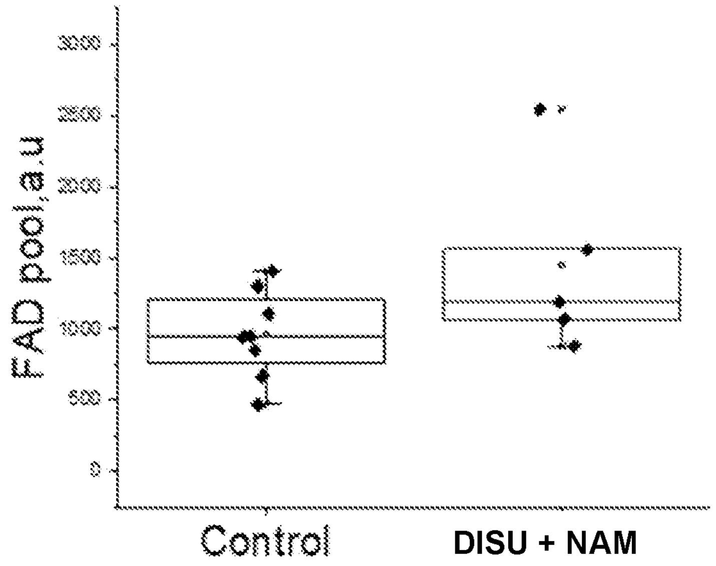
FIG. 3B shows a box plot of representative results of the evaluation of treatment of cultures of primary myotubes with a blend of DiSU and NAM versus a control.

FIGS. 3A and 3B show representative results of the evaluation of treatment of cultures of primary myotubes with a blend of DiSU and NAM (50 μM DiSU+20 μM NAM; the molar ratio choline:succinate:NAM is 2:1:0.4): FIG. 3A shows a graphs of a measurement of autofluorescence of FAD+++ and FIG. 3B shows a plot of and evaluation of the mitochondrial pool of FAD++.

FIG. 4 shows representative results of the evaluation of energetic capability of primary myotubes stimulated to contract with caffeine and either treated or non-treated (control) with a blend of 50 μM DiSU and 20 μM NAM (the molar ratio choline:succinate:NAM is 2:1:0.4). The myotube energetic capability is evaluated as duration of the caffeine stimulated myotube contraction in the presence or absence of DiSU+NAM (i.e., time to collapse of myotube contraction).

What is claimed is:

1. A composition comprising:

nicotinamide (NAM);

creatine or a creatine precursor selected from glycine and arginine; and choline cation and a succinate anion (2−), wherein a molar ratio between the nicotinamide, choline cation and succinate anion (2−) in the composition is between 0.1:2:1 and 1:2:1, correspondingly.

2. The composition of claim 1, wherein the composition comprises dicholine succinate (DiSu).

3. A dietary supplement for a human subject comprising an effective amount of a composition comprising:

nicotinamide (NAM); and choline cation and succinate anion (2−), wherein a molar ratio between the nicotinamide, choline cation and succinate anion (2−) in the composition is between 0.1:2:1 and 1:2:1, correspondingly; and the effective amount comprises 10-1000 mg nicotinamide per serving.

4. The dietary supplement of claim 3, wherein the composition comprises dicholine succinate (DiSu).

5. The dietary supplement of claim 4, wherein the composition further comprises creatine or a creatine precursor selected from glycine and arginine.

6. A composition comprising:

a nicotinamide compound selected from nicotinamide (NAM), nicotinamide riboside (NR), and nicotinamide mononucleotide (NMN); and choline cation and succinate anion (2−), wherein a molar ratio between the nicotinamide compound, choline cation, and succinate anion (2−) in the composition is between 0.1:2:1 and 1:2:1, correspondingly.

7. The composition of claim 6, wherein the composition comprises dicholine succinate (DiSu).

8. The composition of claim 7, wherein the composition further comprises creatine or a creatine precursor selected from glycine and arginine.

9. The composition of claim 8, wherein the nicotinamide compound comprises nicotinamide riboside (NR) or nicotinamide mononucleotide (NMN).

10. The composition of claim 8, wherein the composition is formulated as a beverage.

11. The composition of claim 10, wherein the beverage comprises 10-1000 mg of the nicotinamide compound per serving.

12. The composition of claim 8, wherein the composition is formulated as a dietary supplement.

* * * * *